US008580278B2

(12) United States Patent
Kasper et al.

(10) Patent No.: US 8,580,278 B2
(45) Date of Patent: *Nov. 12, 2013

(54) NUTRACEUTICAL COMPOSITION AND METHODS FOR PREVENTING OR TREATING MULTIPLE SCLEROSIS

(75) Inventors: Lloyd H. Kasper, Norwich, VT (US); Javier Ochoa-Reparaz, Arlington, MA (US)

(73) Assignee: Trustees of Dartmouth College, Hanover, NH (US)

( * ) Notice: Subject to any disclaimer, the term of this patent is extended or adjusted under 35 U.S.C. 154(b) by 69 days.

This patent is subject to a terminal disclaimer.

(21) Appl. No.: 13/162,644

(22) Filed: Jun. 17, 2011

(65) Prior Publication Data

US 2012/0094950 A1    Apr. 19, 2012

Related U.S. Application Data

(63) Continuation-in-part of application No. 12/839,577, filed on Jul. 20, 2010, which is a continuation-in-part of application No. 12/611,627, filed on Nov. 3, 2009, which is a continuation-in-part of application No. PCT/US2009/046074, filed on Jun. 3, 2009.

(51) Int. Cl.
*A61K 39/02* (2006.01)
*A61K 31/715* (2006.01)
*A01N 43/04* (2006.01)

(52) U.S. Cl.
USPC .......................................... 424/234.1; 514/54

(58) Field of Classification Search
USPC .......................................... 424/234.1; 514/54
See application file for complete search history.

(56) References Cited

U.S. PATENT DOCUMENTS

| 5,679,654 | A | 10/1997 | Tzianabos et al. | 514/54 |
|---|---|---|---|---|
| 5,700,787 | A | 12/1997 | Tzianabos et al. | 514/54 |
| 7,083,777 | B1 | 8/2006 | Tzianabos et al. | 424/9.322 |
| 2002/0022019 | A1 | 2/2002 | Laulund | 424/93.45 |
| 2002/0155436 | A1 | 10/2002 | Classen | 435/5 |
| 2003/0219413 | A1 | 11/2003 | Comstock et al. | 424/93.2 |
| 2004/0039056 | A1* | 2/2004 | Bollag et al. | 514/559 |
| 2004/0219160 | A1 | 11/2004 | Tzianabos et al. | 424/184.1 |
| 2005/0271643 | A1 | 12/2005 | Sorokulova et al. | 424/93.462 |
| 2006/0014717 | A1 | 1/2006 | Angstrom et al. | 514/54 |
| 2007/0238747 | A1 | 10/2007 | van Duzer et al. | 514/279 |
| 2008/0286252 | A1 | 11/2008 | Sinnott | 424/93.44 |
| 2009/0124573 | A1 | 5/2009 | Mazmanian et al. | 514/54 |

FOREIGN PATENT DOCUMENTS

| WO | WO 96/07427 | 3/1996 |
|---|---|---|
| WO | WO 00/59515 | 10/2000 |
| WO | WO 02/45708 | 6/2002 |
| WO | WO 2004/089407 | 10/2004 |
| WO | WO 2007/092451 | 8/2007 |
| WO | WO 2009/062132 | 5/2009 |

OTHER PUBLICATIONS

Popovic, N., Schubart, A., Goetz, B.D., Zhang, S.-C., Linington, C., Duncan, I.D. (2002) Inhibition of Autoimmune Encephalomyelitis by a Tetracycline. Annals of Neurology, vol. 51, No. 2, p. 215-223.*
Stromnes, I.M., Goverman, J.M. (2006) Passive induction of experimental allergic encephalomyelitis. Nature Protocols, vol. 1, No. 4, p. 1952-1960.*
Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
"Causes of Multiple Sclerosis" by the Multiple Sclerosis Foundation [online], [Retrieved on Jun. 9, 2011]. Retrieved from the internet <http://www.msfocus.org/causes-multiple.sclerosis.aspx>.*
"Can You Prevent Multiple Sclerosis" by EverydayHealth.com [online], [Retrieved on Jun. 9, 2011]. Retrieved from the internet <http://web.archive.org/web/20090605075946/http://www.everydayhealth.com/multiple-sclerosis/multiple-sclerosis-prevention.aspx>. Published Jun. 4, 2009.*
Mertens, J. et al. (2009) *Streptococcus pneumoniae* Serotype 1 Capsular Polysaccharide Induces CD8+CD28– Regulatory T Lymphocytes by TCR Crosslinking. PLOS Pathogens, vol. 5, No. 9.*
Hori, S., Nomura, T., Sakaguchi, S. (2003) Control of Regulatory T Cell Development by the Transcription Factor Foxp3. Science, vol. 299, p. 1057-1061).*
International Search Report from PCT/US2010/054432, Jan. 18, 2011, PCT.
International Preliminary Report on Patentability from PCT/US2010/054432, May 18, 2012, PCT.
Baumann et al. "Structural Elucidation of Two Capsular Polysaccharides from One Strain of *Bacteroides fragilis* Using High-Resolution NMR Spectroscopy" Biochemistry 1992 31(16):4081-4089.
Kalka-Moll et al. "Immunochemical and Biological Characterization of Three Capsular Polysaccharides from a Single *Bacteroides fragilis* Strain" Infection and Immunity 2001 69(4):2339-2344.
Kalka-Moll et al. "Zwitterionic Polysaccharides Stimulate T Cells by MHC Class II-Dependent Interactions" The Journal of Immunology 2002 168(11):6149-6153.
Mazmanian et al. "A Microbial Symbiosis Factor Prevents Intestinal Inflammatory Disease" Nature 2008 453:620-625.
Tzianabos et al. "The Capsular Polysaccharide of *Bacteroides fragilis* Comprises Two Ionically Linked Polysaccharides" The Journal of Biological Chemistry 1992 267:18230-18235.
Wang et al. "Structural Basis of the Abscess-Modulating Polysaccharide A2 from *Bacteroides fragilis*" Proceedings of the National Academy of Sciences 2000 97(25):13478-13483.

* cited by examiner

*Primary Examiner* — Scarlett Goon
(74) *Attorney, Agent, or Firm* — Licata & Tyrrell, P.C.

(57) ABSTRACT

The present invention embraces nutraceutical compositions containing isolated *Bacteroides fragilis* capsular polysaccharide A for use in methods of preventing or treating multiple sclerosis.

2 Claims, 5 Drawing Sheets

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

His Ser Leu Gly Lys Trp Leu Gly His Pro Asp Lys Phe
1               5                   10

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
ggtcctgtag atggcattgc a                                              21
```

```
<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
ggagctgagc aacatcacac a                                           21
```

NUTRACEUTICAL COMPOSITION AND METHODS FOR PREVENTING OR TREATING MULTIPLE SCLEROSIS

INTRODUCTION

This application is a continuation-in-part of patent application U.S. Ser. No. 12/839,577, filed Jul. 20, 2010, which is a continuation-in-part of patent application U.S. Ser. No. 12/611,627, filed Nov. 3, 2009, which is a continuation-in-part application claiming priority from PCT/US2009/046074, filed Jun. 3, 2009, each of which are herein incorporated by reference in their entireties.

BACKGROUND OF THE INVENTION

*Bacteroides fragilis* is a predominant obligate anaerobe isolated from intra-abdominal abscesses. The capsular polysaccharide complex (CPC) of *B. fragilis* has been identified as the cause of abscess formation (Onderdonk, et al. (1977) *J. Infect. Dis.* 136:82-9; Kasper, et al. (1979) *Rev. Infect. Dis.* 1:278-90; Bergan (1984) *Scand. J. Gastroenterol. Suppl.* 91:1-11). Antibody against the capsular antigen has been shown to provide protection against bacteremia and purified PSA provides protective immunity against abscess formation associated with intra-abdominal sepsis (Kasper and Onderdonk (1982) *Scand. J. Infect. Dis. Suppl.* 31:28-33; Tzianabos, et al. (1994) *Infect Immun.* 62:4881-6; Shapiro, et al. (1982) *J. Exp. Med.* 155:1188-1197). In this respect, *B. fragilis* PSA has been described for use in parenteral pharmaceutical preparations for inducing protection against abscess formation by a variety of bacteria. (U.S. Pat. Nos. 5,679,654 and 5,700,787 and International Patent Applications WO 96/07427, WO 00/59515, and WO 02/45708).

Additional studies have shown that *B. fragilis* PSA modulates various aspects of the immune system. For example, responses to PSA have been shown to involve interleukin 2 and T cell activation to produce Th1-cell-specific cytokines (U.S. Pat. No. 7,083,777). In this respect, conventional pharmaceutical formulations containing PSA have been indicated for parenteral administration to treat an IL-2-responsive disorder by inducing IL-2 secretion or treat a Th1-cell-responsive disorder such as insulin-dependent diabetes mellitus, experimental allergic encephalomyelitis, inflammatory bowel disease, and allograft rejection by activating T cells (U.S. Pat. No. 7,083,777 and International Patent Application WO 2009/062132).

Moreover, it has been shown that purified *B. fragilis* PSA can provide protection from trinitrobenzene sulphonic acid (TNBS)-induced intestinal colitis and inhibit inflammation and death associated with systemic septic shock (U.S. Patent Application No. 20090124573). As such, conventional pharmaceutical compositions containing purified PSA have been indicated for oral, subcutaneous, intraperitoneal, or intravenous administration to control an inflammation associated with an imbalance of T-helper cell profile and in particular to a Th17 cell profile, e.g., in rheumatoid arthritis, respiratory diseases, allograft rejection, systemic lupus erythematosis, tumorgenesis, multiple sclerosis, systemic sclerosis and chronic inflammatory bowel disease (U.S. Patent Application No. 20090124573).

Similarly, U.S. Patent Application No. 20040219160 and International Patent Application WO 2004/089407 describe conventional pharmaceutical compositions, preferably aerosols, containing *B. fragilis* polysaccharide A and similar polymers for use in treating and protecting against asthma and allergic conditions.

A nutritional formula or nutritional supplement composition containing isolated zwitterionic polysaccharide such as *B. fragilis* PSA, preferably for enteral administration, is also described for use in promoting immune system maturation (International Patent Application WO 2007/092451). Such preparations are disclosed as being dry or water-based formulations containing any one or combination of nutritional carbohydrates, amino acids and proteins, fats, vitamins, minerals, and optionally other components such as nucleic acids. While capsules and pills are particularly described, other formulations are also mentioned, including bars, sprinkles, cereals, gels, and pastes.

In addition to modulating immune responses, *B. fragilis* have been suggested for use in processing natural polysaccharides into useful products that have utility as dietary supplements or foods polysaccharides (U.S. Patent Application No. 20080286252).

Given the significant immunomodulatory effects of *B. fragilis* PSA, a consumable nutraceutical composition of *B. fragilis* PSA is disclosed herein for use in the prevention of treatment of disease, in particular multiple sclerosis.

SUMMARY OF THE INVENTION

The present invention features nutraceutical compositions composed of isolated *B. fragilis* capsular PSA and a nutritional source, preferably for oral consumption by a human subject. In one embodiment the PSA is purified. In another embodiment, the nutraceutical is a food product, foodstuff, functional food, or a supplement composition for a food product or a foodstuff. In some embodiments, the amount of *B. fragilis* PSA is 10 mg to 1000 mg per serving or alternatively 50 mg to 500 mg per serving. In particular embodiments, the nutraceutical composition is configured to prevent or treat multiple sclerosis. A nutraceutical composition, wherein the nutritional source modulates endogenous commensal bacterial populations, is provided as are commercial packages containing nutraceutical compositions of the invention.

The present invention also embraces a method for preventing or treating multiple sclerosis. This method involves administering to a subject in need of treatment an effective amount of isolated, and optionally purified, *B. fragilis* PSA alone or in combination with an antibiotic so that multiple sclerosis is prevented or treated.

The present invention also includes a method for stimulating FoxP3+ regulatory T cell expression of CD39 by contacting FoxP3+ regulatory T cells with an effective amount of isolated, and optionally purified, *B. fragilis* PSA alone or in combination with a retinoic acid.

DETAILED DESCRIPTION OF THE INVENTION

Figure 1:
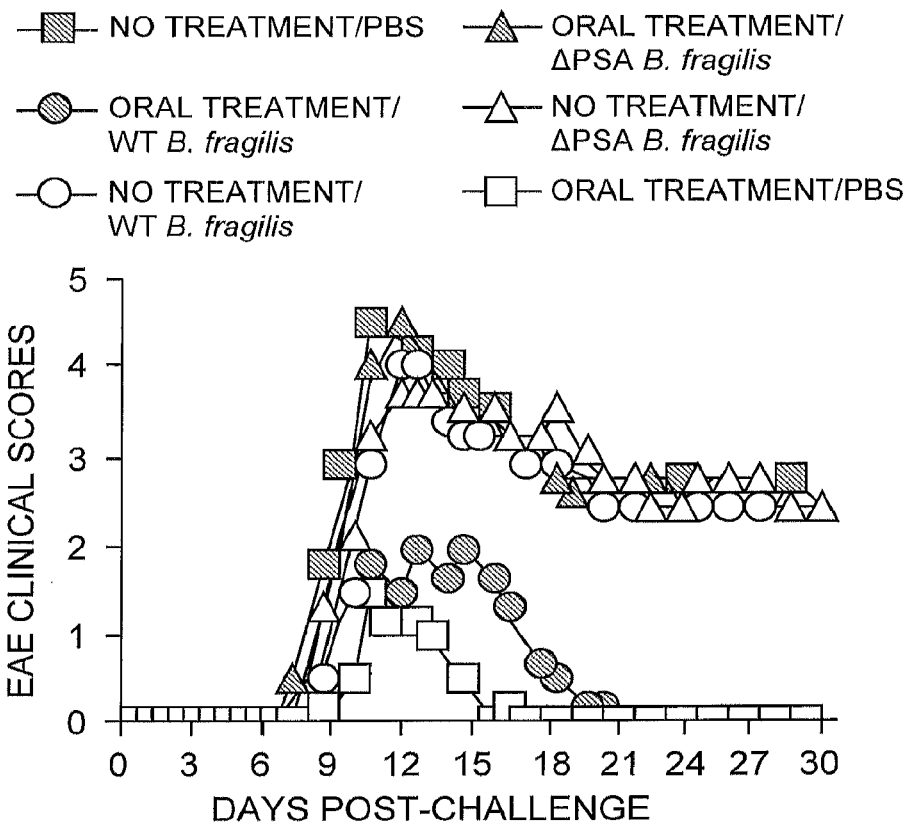
FIG. 1 shows that antibiotic treatment against gut microflora, as well as subsequent reconstitution with wild-type *B. fragilis* reduces EAE clinical scores.

It has now been demonstrated that B. fragilis PSA induces a population of CD4+CD39+ T regulatory cells, cells shown to be deficient in subjects with multiple sclerosis, and also confers prophylactic and therapeutic protection against EAE, the experimental model of multiple sclerosis. Accordingly, the present invention embraces nutraceutical compositions containing isolated B. fragilis. PSA and use of such nutraceutical compositions in methods for the inducing populations of CD4+CD39+ T regulatory cells and preventing and/or treating of multiple sclerosis.

B. fragilis PSA as used herein refers to a molecule produced by the PSA locus of B. fragilis. PSA of use in the instant invention can be PSA1 and/or PSA2. PSA1 is composed of a tetrasaccharide repeating unit containing 4,6-pyruvate attached to a D-galactopyranose, 2,4-dideoxy-4-amino-D-FucNAc, D-N-acetylgalactosamine, and D-galactofuranose (Tzianabos, et al. (1992) J. Biol. Chem. 267:18230-5; Baumann, et al. (1992) Biochemistry 31(16):4081-9; U.S. Pat. Nos. 5,679,654 and 5,700,787). PSA2 refers to B. fragilis capsular polysaccharide A as disclosed, for example, in Wang, et al. (2000) Proc. Natl. Acad. Sci. USA 97:13478-83, and Kalka-Moll, et al. (2001) Infect. Immun. 69:2339-44. B. fragilis PSA2 has a pentasaccharide repeating unit containing mannohептose, N-acetylmannosamine, 3-acetamido-3,6-dideoxyglucose, 2-amino-4-acetamido-2,4,6-trideoxy galactose, fucose, and 3-hydroxybutanoic acid.

In particular embodiments, the B. fragilis PSA is isolated from a natural source. In this respect, B. fragilis PSA can be isolated from wild-type B. fragilis (i.e., a B. fragilis that has not been modified by recombinant techniques) or a B. fragilis strain that overexpresses PSA (see, U.S. Pat. No. 7,166,455). Wild-type B. fragilis can be obtained commercially from a number of sources. For example, strains NCTC 9343 and ATCC 23745 can be obtained from the National Collection of Type Cultures (London, England) and the American Type Culture Collection (Manassas, Va.), respectively.

PSA can be isolated, and in some embodiments purified, from B. fragilis following the protocol of Baumann, et al. (1992) supra; Kalka-Moll, et al. (2002) J. Immunol. 169(11): 6149-53; Tzianabos, et al. (1992) J. Biol. Chem. 267:18230-18235; or Pantosti, et al. (1991) Infect. Immun. 59:2075-2082. By way of illustration, B. fragilis is grown in a fermenter and the cells are harvested by centrifugation and suspended in water. An equal volume of phenol is added, and the mixture is heated to 60° C. for 30 minutes. The resultant aqueous phase is extracted with ether, concentrated, and treated with DNase, RNase, and pronase. This concentrate is chromatographed on a column of SEPHACRYL S-300 in a buffer containing 0.5% sodium deoxycholate and capsular polysaccharide fractions subsequently separated by DEAE-SEPHACEL. The purity of PSA can be assessed by SDS/PAGE, ¹H-NMR spectroscopy, and/or UV wavelength scans.

Isolated B. fragilis PSA means that the PSA has been removed from at least one component with which PSA may be found in nature. In this respect, B. fragilis PSA is isolated in the sense that it is prepared as an extract of B. fragilis, e.g., a cell wall extract or culture medium extract. In nature, PSA occurs in a dimerized form, tightly bound to the B. fragilis capsular polysaccharide B. Thus, in some embodiments, the B. fragilis is free from dimerization as part of a B. fragilis capsular polysaccharide complex. In particular embodiments, B. fragilis PSA is purified. Purified B. fragilis PSA refers to PSA that is 80%, 85%, 90%, 95%, 96%, 97%, 98%, 99%, 99.5% or 99.9% homogeneous to PSA.

Isolated and optionally purified B. fragilis PSA can be used in its natural form or modified to increase activity, stability or shelf-life. A naturally occurring B. fragilis PSA as used herein refers to a B. fragilis PSA that is not modified from how it occurs in nature except for being isolated. A modified PSA refers to a polysaccharide that is structurally related to PSA and is derivable from PSA by a modification that introduces a feature that is not present in PSA while retaining functional properties of PSA. Accordingly, a modified PSA, usually differs from the original polysaccharide by modification of the repeating units or of the saccharidic component of one or more of the repeating units that might or might not be associated with an additional function not present in the original polysaccharide. A modified PSA retains however one or more functional activities that are herein described in connection with PSA in association with the protective activity of PSA. Examples of modifications to PSA include oxidation with 0.01 M sodium metaperiodate by the procedure of Teleti, et al. ((1992) J. Clin. Invest. 89:203-209), which has been shown to enhance biological activity. This modification selectively creates carbonyl groups (C═O) on the galactofuranose side chain of the PSA repeating unit, which are amenable to reduction with a reducing agent such as sodium borohydride and conversion to a hydroxymethyl group. PSA can also or alternatively be modified at the C-5 position of the furanoside to include a hydroxymethyl group (See, e.g., U.S. Pat. No. 5,679,654).

To promote the prophylactic and therapeutic benefits associated with PSA in a readily available, GRAS (Generally Recognized As Safe) formulation, the present invention embraces a nutraceutical composition composed of isolated, and optionally purified, *B. fragilis* PSA in combination or admixture with a nutritional source. As appreciated by those skilled in the art, a nutraceutical composition refers to a food (or part of a food) that provides medical or health benefits, including the prevention and/or treatment of a disease. See, e.g., Brower (1998) *Nat. Biotechnol.* 16:728-731; Kalra (2003) *AAPS PharmSci.* 5(3):25. In this respect, not only does the instant nutraceutical composition provide a nutritional source, it is also configured to provide prophylactic and therapeutic benefit against multiple sclerosis.

As appreciated by one skilled in the art, a nutraceutical composition is distinct from a dietary or nutritional supplement. The Dietary Supplement Health and Education Act of 1994 defines dietary supplements as products intended to supplement the diet. In addition, dietary supplements are not represented for use as a conventional food or as a sole item of a meal or the diet. In this respect, nutraceutical compositions differ from dietary supplements or nutritional supplement in the following aspects: nutraceuticals must not only supplement the diet but should also aid in the prevention and/or treatment of disease and/or disorder; and nutraceuticals are represented for use as a conventional food or as the sole item of meal or diet. See, e.g., Kalra (2003) supra.

Thus, a nutraceutical composition of the invention not only provides isolated, and optionally purified, *B. fragilis* PSA, but also provides a nutritional source. Accordingly, a nutraceutical composition of the invention can be a food product, foodstuff, functional food, or a supplement composition for a food product or a foodstuff. As used herein, the term food product refers to any food or feed which provides a nutritional source and is suitable for oral consumption by humans or animals. The food product may be a prepared and packaged food (e.g., mayonnaise, salad dressing, bread, or cheese food) or an animal feed (e.g., extruded and pelleted animal feed, coarse mixed feed or pet food composition). As used herein, the term foodstuff refers to a nutritional source for human or animal oral consumption. Functional foods are defined as foods being consumed as part of a usual diet but are demonstrated to have physiological benefits and/or reduce the risk of chronic disease beyond basic nutritional functions.

Food products, foodstuffs, or functional foods are for example beverages such as non-alcoholic and alcoholic drinks as well as liquid preparations to be added to drinking water and liquid food. Non-alcoholic drinks are for instance soft drinks; sport drinks; fruit juices, such as orange juice, apple juice and grapefruit juice; lemonades; teas; near-water drinks; and milk and other dairy drinks such as yogurt drinks, and diet drinks. In other embodiments food products, foodstuffs, or functional foods refer to solid or semi-solid foods. These forms can include, but are not limited to, baked goods such as cakes and cookies; puddings; dairy products; confections; snack foods (e.g., chips); or frozen confections or novelties (e.g., ice cream, milk shakes); prepared frozen meals; candy; liquid food such as soups; spreads; sauces; salad dressings; prepared meat products; cheese; yogurt and any other fat or oil containing foods; and food ingredients (e.g., wheat flour).

It is understood by those of skill in the art that in additional to isolated, and optionally purified, *B. fragilis* PSA and a nutritional source, other ingredients can be added to food products, foodstuffs, or functional foods described herein, for example, fillers, emulsifiers, preservatives, etc. for the processing or manufacture of the same. Additionally, flavors, coloring agents, spices, nuts and the like may be incorporated into the nutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, extracts such as pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; volatile oils, such as balm oil, bay oil, bergamot oil, cedarwood oil, walnut oil, cherry oil, cinnamon oil, clove oil, or peppermint oil; peanut butter; cocoa; chocolate flavoring; vanilla cookie crumb; butterscotch or toffee.

Emulsifiers can also be added for stability of the nutraceutical compositions. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives can also be added to the nutritional supplement to extend product shelf life. Preferably, preservatives such as potassium sorbate, sodium sorbate, potassium benzoate, sodium benzoate or calcium disodium EDTA are used.

In addition, the nutraceutical composition can contain natural or artificial (preferably low calorie) sweeteners, e.g., saccharides, cyclamates, aspartamine, aspartame, acesulfame K, and/or sorbitol. Such artificial sweeteners can be desirable if the nutraceutical composition is intended to be consumed by an overweight or obese individual, or an individual with type II diabetes who is prone to hyperglycemia.

Moreover, a multi-vitamin and mineral supplement can be added to the nutraceutical compositions of the present invention to obtain an adequate amount of an essential nutrient, which is missing in some diets. The multi-vitamin and mineral supplement can also be useful for disease prevention and protection against nutritional losses and deficiencies due to lifestyle patterns.

As described herein, modulation of commensal bacterial populations can provide additional benefit against the development and progression of EAE and hence human multiple sclerosis. Accordingly, particular embodiments of the invention provide for the nutritional source of the nutraceutical to modulate endogenous commensal bacterial populations. Such modulation can be achieved by modification of gut pH, consumption of beneficial bacteria (e.g., as in yogurt), by providing nutritional sources (e.g., prebiotics) that select for particular populations of bacteria, or by providing antibacterial compounds. Such modulation can mean an increase or decrease in the gut microbiota populations or ratios. In particular embodiments, the absolute or relative numbers of desirable gut microorganisms is increased and/or the absolute or relative numbers of undesirable gut microorganisms is decreased. For example, it is contemplated that there are a variety of nutritional sources exhibiting antibacterial activity that can be used to modulate gut microbiota populations. For example, garlic has been shown to produce the compound allicin (allyl 2-propenethiosulfinate), which exhibits antibacterial activity toward *E. coli* (Fujisawa, et al. (2009) *Biosci. Biotechnol. Biochem.* 73(9):1948-55; Fujisawa, et al. (2008) *J. Agric. Food Chem.* 56(11):4229-35). Similarly, rosemary extracts and other essential oils have been shown to contain antibacterial activity (Klancnik, et al. (2009) *J. Food Prot.*

72(8):1744-52; Si, et al. (2006) *J. Appl. Microbiol.* 100(2): 296-305). Extracts of the edible basidiomycete, *Lentinus edodes* (Shiitake), have also been shown to possess antibiotic activity (Soboleva, et al. (2006) *Antibiot. Khimioter.* 51(7):3-8; Hirasawa, et al. (1999) *Int. J. Antimicrob. Agents* 11(2): 151-7). Moreover, purple and red vegetable and fruit juices exhibit antibacterial activities (Lee, et al. (2003) *Nutrition* 19:994-996).

The nutraceutical composition of the present invention can be provided in a commercial package, alone, or with additional components, e.g., other food products, food stuffs or functional foods for preparing a complete meal. Desirably, the commercial package has instructions for consumption of the instant nutraceutical, including preparation and frequency of consumption, and use in the prevention or treatment of multiple sclerosis. Moreover, in particular embodiments, the commercial package further includes a natural product (e.g., the food, extracts, and oils disclosed herein) that modulates endogenous commensal bacterial populations. A package containing both a nutraceutical of the invention in combination with said natural product can contain instructions for consuming the natural product, e.g., in advance (e.g., 2, 4, 6 or 8 or more hours) of consuming the nutraceutical in order to enhance the activity of the nutraceutical composition.

The data presented herein demonstrate a significant reduction in the severity of EAE of mice treated orally with PSA before and after EAE induction. Accordingly, the present invention also features a method for treatment, co-treatment, and/or prevention of multiple sclerosis, in animals including humans. The method of this invention involves the step of administering an effective amount of isolated *B. fragilis* PSA to a subject in need thereof, so that the subject receives prophylactic or therapeutic benefit. In this respect, prevention, as used herein, means that a disease does not develop or is attenuated as a result of the administration of the therapeutic agent, whereas treatment means a decrease in progression, reversal or amelioration of one or more signs or symptoms of the disease being treated. For example, a subject benefiting from receiving PSA would exhibit attenuation, prevention, delay, reversal, or amelioration of one or more signs or symptoms of MS including, but not limited to, demyelination; nucleated cell infiltration; muscle weakness, abnormal muscle spasms, or difficulty in moving; ataxia; dysarthria or dysphagia, nystagmus, optic neuritis, diplopia, acute or chronic pain syndromes, or bladder and bowel difficulties. Such outcomes are described herein and can be routinely determined by the skilled clinician. Subjects in need of treatment with isolated *B. fragilis* PSA include those diagnosed with MS as well as subjects predisposed to the development of multiple sclerosis, e.g., those with a deficiency of vitamin D during childhood (Munger, et al. (2006) *JAMA* 296:2832-8).

In addition to PSA, particular embodiments of the invention embrace co-treatment of subjects with one or more antibiotics to enhance the activity of PSA. Desirably, the at least one antibiotic is administered prior to administration of the PSA so that the commensal bacterial population of the subject is modulated. Antibiotics of use in this embodiment can include antibiotics present in natural products, or conventional antibiotics such as those disclosed herein (i.e., ampicillin, vancomycin, neomycin sulfate and metronidazole) as well as any other suitable antibiotic including, but not limited to, Amoxicillin, Alatrofloxacin, Tetracycline, Moxifloxacin, Azithromycin, Bacampicillin, Oxacillin, Benzylpenicillin, Clarithromycin, Carbenicillin, Cefadroxil, Cephalexin, Cefditoren, Cefepime, Cefmetazole, Cefoperazone, Cefprozil, Cephalexin, Clarithromycin, Clindamycin, Daptomycin, Dicloxacillin, Erythromycin, Gemifloxacin, Sulfamethoxazole, Kanamycin, Levofloxacin, Lincomycin, Lomefloxacin, Vancomycin, Meropenem, Nafcillin, Nalidixic Acid, Tobramycin, Piperacillin, Polymyxin, Trimethoprim, Rifampin, Streptomycin, Trovafloxacin, and combinations thereof. In so far as extended administration (e.g., 2, 3, 4 or more weeks) has been shown to confer full protection against EAE in mice, antibiotic(s) can be administered in single or multiple doses for acute or chronic periods of time. The amount of antibiotic employed desirably reduces bacterial load, the gut microbiota composition, or ratios of particular species of bacteria. While the antibiotic can be administered via any suitable route, particular embodiments embrace oral administration. Moreover, the antibiotic and PSA can be administered simultaneously or consecutively (e.g., within a day, week or month of one another).

The dose of isolated *B. fragilis* PSA administered according to this invention will, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can be determined by the expert in the field with normal trials, or with considerations regarding the formulation of the PSA, e.g., as a pharmaceutical or a nutraceutical composition.

Based upon the results presented herein, wherein mice of an average weight of 50 g benefited from a 50 to 100 μg amount of isolated *B. fragilis* PSA administered every three days, a human subject (average weight of 70 kg) would receive benefit from a 70 to 140 mg amount of isolated *B. fragilis* PSA. Accordingly, in particular embodiments, the instant invention embraces an amount of 10 mg to 1000 mg, or more desirably 50 mg to 500 mg of isolated *B. fragilis* PSA be administered or consumed per dose or per serving. In some embodiments, a minimum amount of 150 mg per serving is employed. In other embodiments, a minimum amount of 200 mg per serving is employed. The term "serving" as used herein denotes an amount of food or beverage normally ingested by a human adult with a meal at a time and may range, e.g., from about 50 g to about 500 g.

Given that the instant PSA is obtained from a commensal bacterium, frequent consumption of a nutraceutical composition of the present invention is expected to provide prophylactic and therapeutic benefit, while avoiding possible toxic side effects due to increased administration. Therefore, daily consumption of the instant nutraceutical composition is contemplated. In this respect, not only does the present invention embrace consumption of the instant nutraceutical once, twice, or three times per week, particular embodiments embrace consumption of the instant nutraceutical at least one time per day, two times per day or three times per day.

No significant differences in the numbers of $T_{reg}$ cells are observed between multiple sclerosis patients and healthy controls. However, the suppressive function of $T_{reg}$ cells from multiple sclerosis patients appears to be reduced when compared to those obtained from healthy individuals (Haas, et al. (2005) *Euro. J. Immunol.* 35:3343-3352). It has been suggested that ATP hydrolytic function of CD39+ $T_{reg}$ cells is impaired in multiple sclerosis patients. As demonstrated herein, FoxP3+ $T_{reg}$ cells contacted with PSA and optionally retinoic acid acquire the CD39+ phenotype. Thus, in addition to oral consumption of PSA in the treatment of multiple sclerosis, it is contemplated that subjects with multiple sclerosis could benefit from receiving autologous, syngeneic or allogeneic FoxP3+ $T_{reg}$ cells that have been contacted with PSA or PSA in combination with retinoic acid. Accordingly, the present invention also includes the use of isolated, and optionally purified, PSA or PSA in combination with retinoic acid to stimulate FoxP3+ regulatory T cell expression of CD39. According to this method of the invention, FoxP3+ regulatory T cells are contacted with an effective amount of PSA, and in some embodiments retinoic acid, so that expression of CD39 is stimulated, enhanced or increased as compared to FoxP3+ regulatory T cells which have not been contacted with PSA or retinoic acid. In this respect, FoxP3+ $T_{reg}$ cells can be harvested by conventional means, optionally expanded, contacted with PSA (and in some embodiments, retinoic acid) to acquire the CD39+ phenotype, and adoptively transferred into a subject with multiple sclerosis. Alternatively, FoxP3+ $T_{reg}$ cell precursors can be isolated and used in the preparation of FoxP3+ CD39+ $T_{reg}$ cells. In the context of this method of invention, an effective amount of PSA or PSA and retinoic acid is an amount which results in a measurable increase in CD39 expression in FoxP3+ $T_{reg}$ cells as compared to FoxP3+ $T_{reg}$ cells not contacted with PSA or PSA and retinoic acid. In this respect, the effectiveness of PSA or PSA and retinoic acid for increasing or enhancing CD39 expression can be determined by measuring CD39 expression, e.g., by cell sorting or western blot analysis, prior to adoptive transfer of the cells into a subject with multiple sclerosis. Methods of obtaining and using freshly isolated or ex vivo expanded donor-derived $T_{reg}$ cells is known in the art, e.g., in delaying or preventing immune responses such as graft versus host disease (Cohen, et al. (2002) *J. Exp. Med.* 196:401-6; Edinger, et al. (2003) *Nature Med.* 9:1144-50; Taylor, et al. (2002) *Blood* 99:3493-9), and can be readily adapted for use in accordance with this invention in the treatment of multiple sclerosis. Moreover, adoptive transfer of FoxP3+ CD39+ $T_{reg}$ cells can be combined with conventional multiple sclerosis therapeutics such as IFN-β and glatiramer acetate, as well as therapeutics under evaluation, e.g., alemtuzumab, that enhance numbers and anti-inflammatory function of $T_{reg}$ cells in EAE and multiple sclerosis (Korporal, et al. (2008) *Arch. Neurol.* 65:1434-1439; Pascual, et al. (2008) *Am. J. Transplant* 8:1529-1536; Stasi, et al. (2008) *Blood* 112:1147-1150).

The invention is described in greater detail by the following non-limiting examples.

Example 1

Materials and Methods

Mice.

Female, six-week old SJL/J mice were obtained from The Jackson Laboratories (Bar Harbor, Me.). All mice were maintained under pathogen-free conditions in individual ventilated cages under HEPA-filtered barrier conditions and were fed sterile food and water ad libitum.

Oral Immunizations with Purified PSA.

Mice were treated orally with 50 μg or 100 μg of purified PSA.

Antibiotic Treatments in Drinking Water and Bacterial Reconstitution.

SJL mice were treated with the following antibiotics dissolved in drinking water: Ampicillin (1 g/ml), vancomycin (0.5 g/ml), neomycin sulfate (1 g/ml) and metronidazole (1 g/ml) (Rakoff-Nahoum, et al. (2004) *Cell* 118:229-41). When required, dissolved antibiotics were administered by i.p. injections at daily single doses of 1 g/ml. Serial dilutions of intestinal and fecal samples were cultured in general bacteriological agar plates (CDC blood agar; BD, Sparks, MD) for 48 hours at 37° C. Plates were cultured in aerobic and anaerobic conditions. Total bacteria/gram of sample was calculated based on the colony forming units (CFU) counted in each serial dilution.

Wild-type *Bacteroides fragilis* (WT *B. fragilis*) (NCTC 9343) and PSA-deficient *B. fragilis* (ΔPSA *B. fragilis*) are known in the art (Mazmanian, et al. (2005) *Cell* 122:107-118). Mice were infected with $10^{10}$ WT or ΔPSA *B. fragilis* resuspended in 200 μl of sterile PBS by oral gavage.

Microarray Analysis of Commensal Bacteria Populations.

Fresh fecal samples of mice were collected on days 0 and 7 of treatment with antibiotics, and day 7 after reconstitution with WT or ΔPSA *B. fragilis*. Samples were snap frozen and stored at −80° C. Total DNA from mice fecal samples was obtained using a modified extraction protocol of the QIAMP DNA Stool mini kit (QIAGEN Inc., Valencia, Calif.). Extraction yields and DNA concentrations were measured with a NANODROP ND-1000 spectophotometer (NanoDrop Technologies, Wilmington, Del.). The microarray analysis of small subunit ribosomal RNA (SSU rRNA) gene sequences of commensal bacteria populations was carried out according to standard conditions (Fiocco, et al. (2009) *J. Bacteriol.* 191(5):1688-94; Troost, et al. (2008) *BMC Genomics* 9:374).

$PLP_{139-151}$ Challenge. The encephalitogenic PLP peptide ($PLP_{139-151}$; HSLGKWLGHPDKF; SEQ ID NO:1) was synthesized by Peptides International (Louisville, Ky.), and HPLC-purified to >90%. For each experiment, female SJL mice (4/group) were challenged s.c. with 200 μg $PLP_{139-151}$ in 200 μl of Complete Freunds Adjuvant (Sigma). On days 0 and 2 post-challenge, mice received i.p. 200 ng of *Bordetella pertussis* toxin (PT; List Biological Laboratories, Campbell, Calif.) (Ochoa-Reparaz, et al. (2007) *J. Immunol.* 178:1791-9). Control groups were treated with PBS. Mice were monitored and scored daily for disease progression (Ochoa-Reparaz, et al. (2007) supra): 0, normal; 1, a limp tail; 2, hind limb weakness; 3, hind limb paralysis; 4, quadriplegia; 5, death.

Histological Evaluation of Spinal Cords.

For histological evaluation, spinal cords were harvested 12 days after challenge and fixed with neutral buffered formalin (VWR International, West Chester, Pa.), embedded into paraffin, and sectioned at 3 μm. Transverse sections of spinal cords were stained with H&E for pathological changes and inflammatory cell infiltration. Adjacent sections were stained with luxol fast blue (LFB) and examined for loss of myelin. Pathological manifestations were scored separately for cell infiltrates and demyelination. Each H&E section was scored from 0 to 4: 0, normal; 1, cell infiltrate into the meninges; 2, one to four small focal perivascular infiltrates; 3, five or more small focal perivascular infiltrates and/or one or more large infiltrates invading the parenchyma; 4, extensive cell infiltrates involving 20% or more of the white matter (Ochoa-Reparaz, et al. (2007) supra). In each LFB stained section, myelin was also scored from 0 to 4: 0, normal; 1, one small focal area of demyelination; 2, two or three small focal areas of demyelination; 3, one to two large areas of demyelination; 4, extensive demyelination involving 20% or more of white matter.

Cytokine Detection by LUMINEX Spleens and cervical lymph nodes (CLNs) were aseptically harvested from naïve mice and from mice treated with antibiotics for 7 days. Cell suspensions were resuspended in complete medium (CM): RPMI 1640 medium supplemented with 1 mM sodium pyruvate, 1 mM nonessential amino acids (Gibco), penicillin/streptomycin (10 U/ml) (Gibco), and 10% fetal bovine serum (Atlanta Biologicals, Lawrenceville, Ga.). Lymphocytes were cultured in 24-well tissue plates at $2 \times 10^6$ cells/ml in CM alone or in the presence of anti-CD3 mAb-coated wells (10 μg/ml; BD Pharmingen), plus the soluble anti-CD28 mAb (5.0 µg/ml; BD Pharmingen) for 3 days in CM (final volume of 300 µl in 24-wells plate) (Ochoa-Reparaz, et al. (2007) supra). LUMINEX was employed to quantify triplicate sets of samples to measure IFN-γ, TNF-α, MIP-1α, MIP-1β, MCP-1, IL-6, IL-17, IL-4, IL10, and IL-13 cytokines.

PCR Detection of Cytokine mRNA.

A total of 1.0 µg of QIAGEN RNEASY-purified (QIAGEN) mRNA was reverse-transcribed using MULTI-SCRIBE RT (Amersham Biosciences AB, Uppsala, Sweden). A total of 200 ng of cDNA was amplified using the x2 SYBR green mix (Applied Biosystems) on a BIO-RAD iCycler. Relative expression was normalized to β-actin and was expressed using the CT method, where relative expression=2^(exp-actin)*1000. PCR detection of IL-13 mRNA was carried out with primers 5'-GGT CCT GTA GAT GGC ATT GCA-3'(SEQ ID NO:2) and 5'-GG AGC TGA GCA ACA TCA CAC A-3' (SEQ ID NO:3).

FACS Analysis.

Lymphocytes from the Peyer's Patches (PPs), MLNs, spleens and CLNs were isolated from naïve mice, mice treated with antibiotics, and treated with antibiotics and subsequently colonized with wild-type $B.\ fragilis$ or ΔPSA $B.\ fragilis$ 12 days after challenge with $PLP_{139-151}$, and single cell preparations were prepared according to standard methods (Ochoa-Reparaz, et al. (2007) supra). Cells were stained for FACS analysis using conventional methods. T cell subsets were analyzed using fluorochrome-conjugated mAbs (BD Pharmingen) for CD3, CD4, CD8, CD45Rb and CD25 as indicated. Intracellular staining for FoxP3 and IFN-γ, IL-17, IL-13, IL10, IL-4 cytokines were performed using fluorochrome labeled-anti-Foxp3 mAb (clone FJK-16s; eBioscience, San Diego, Calif.) and PE labeled-anti-IFN-γ, IL-17, IL10, IL-4 (BD Pharmingen) and anti-IL-13 (eBiosciences). For macrophages and dendritic cell subpopulations, CD11b, CD11c, CD103, B220, CD8, Gr-1 and F4/80 mAb were used. ((BD Pharmingen). For NK cells, DX5, B220 and CD11b were used. For B cells, CD19 and B220 (BD Pharmingen) were used. Bound fluorescence was analyzed with a FACS Canto (BD Biosciences, Mountain View, Calif.).

Retinoic Acid Detection in Tissues.

Retinoic acid was detected in PPs and MLNs according to standard protocols (Wagner (1997) $Methods\ Enzymol.$ 282: 98-107). Briefly, a monolayer of retinoid reporter cell line was co-cultured with whole PPs overnight at 37° C. with 5% $CO_2$. After incubation, tissues were removed and cells were treated for 1 minute at 37° C. with FITC staining for gene reporter, and analyzed by FACS (Wagner (1997) $Methods\ Enzymol.$ 282:98-107). The RA-inducible reporter cell line used was a lacZ reporter line derived from F9 teratocarcinoma cells transfected with an $E.\ coli$ β-galactosidase reporter gene. This gene product is encoded under the control of a known retinoid response. Reporter enzymatic activity indicates the presence of retinoids released from sample tissues.

Cell Purifications.

CD11c+ cells were obtained with magnetic beads (StemCell Technologies, Vancouver, Canada). The enriched $CD11c^+$ cells were cell-sorted (FACSVANTAGE with Turbo-Sort, BD Biosciences) following staining with FITC-anti-CD103 into $CD11c^{high}CD103^+$ cells. $CD4^+$ T cells and $CD8^+$ T cells were obtained with magnetic beads (Dynal Biotech ASA, Oslo, Norway). The enriched $CD4^+$ T cells were cell-sorted for FITC-anti-CD4 and APC-anti-CD25 mAbs (BD PharMingen) by FACS.

In Vitro Suppressive Assays and Adoptive Transfer Experiments.

Naïve CD25-CD4+ T cells ($1.5 \times 10^5$) were co-cultured in triplicate with $CD11c^{high}CD103^+$ in the presence or absence of retinoic acid (4 nM) and TGF-β (5 ng/ml). Anti-CD3 mAb (10 mg/ml; BD Pharmingen) and IL-2 (20 units/well) were added. Cells were incubated at 37° C. in 5% of $CO_2$ for 72 hours. Conversion of naïve $CD25-CD4^+$ T cells into $FoxP3^+$ $T_{reg}$ cells was compared by FACS. To assess $T_{reg}$ cell suppressor activity, $1.5 \times 10^5$ responder $CD25-CD4^+$ T cells were labeled with CFSE and subsequently co-cultured in triplicate with $CD25^+CD4^+$ T cells at 1:1, 1:0.1, 1:0.01 and 1:0.001 $CD25^-:CD25^+$ T cell ratios. Feeder cell (T cell-depleted mitomycin C-treated) splenocytes prepared from naïve mice (Pascual, et al. (1999) $Infect.\ Immun.$ 67:6249-56) were added at $1.5 \times 10^5$ cells per well. Cells were incubated at 37° C. in 5% of $CO_2$ for 72 hours. $CD4^+$ T cell proliferation was compared by FACS. For adoptive transfer experiments, $4 \times 10^5$ $CD25^+CD4^+$ T cells or $CD25^-CD4^+$ T cells were i.v. injected into naïve recipients. One day after the adoptive transfer of T cells, mice were challenged with $PLP_{139-151}$ to induce EAE.

In Vivo Inactivation of $CD25^+CD4^+$ T Cells.

Mice were orally treated with antibiotics seven days prior to EAE challenge with $PLP_{139-151}$ and PT. To inactivate $CD25^+CD4^+$ T cells, the same mice were given 0.3 mg of anti-CD25 mAb (ATCC #TIB-222, clone PC 61.5.3) on days 4 and 2 before EAE challenge (Ochoa-Reparaz, et al. (2007) supra). As a control group, treated and naïve mice received 0.3 mg of purified rat IgG antibody on the same days prior to EAE challenge. CD25 depletion was confirmed by FACS analysis of peripheral blood samples obtained 2 days after the administration of the second dose of anti-CD25 or rat IgG antibodies. A separate control group was immunized with PBS seven days prior to EAE challenge.

Statistical Analysis.

The student t test was applied to show differences of combined experiments in clinical scores, body, spleen and cecum weights, LUMINEX detection of cytokines as well as in the flow cytometry of $T_{reg}$ cell and DC experiments. ANOVA followed by post-hoc Tukey test was applied to show differences in EAE clinical scores. P-values <0.05 and <0.01 are indicated.

Example 2

Oral Treatment with Antibiotics Reduces Commensal Microflora and Alters Immune Responses in the GALT and the Periphery C57BL/6 and SJL mice were treated with antibiotics in order to reduce the gut bacterial population (Wagner (1997) $Methods\ Enzymol.$ 282:98). Ampicillin (1 g/ml), vancomycin (0.5 g/ml), neomycin sulfate (1 g/ml) and metronidazole (1 g/ml) were dissolved in drinking water and supplied to mice for seven days. Oral treatment with antibiotics reduced bacterial PFU by day 4-post treatment and significantly reduced the commensal populations from the fecal and intestinal samples of mice. Aerobic and anaerobic conditions were examined and in both cases, a significant reduction of bacterial counts was found one week after treatment. No bacterial CFU were detected in fecal samples of mice treated orally with antibiotics as opposed to the culture of fecal intestinal contents, suggesting that fresh pellets might be insufficient in order to compare total bacterial loads. Only oral but not i.p. treatment, with antibiotics reduced gut commensal microflora and altered significantly the morphology of the mice.

However, antimicrobial treatment did not completely deplete bacterial presence showing that certain bacterial populations remain viable despite antibiotic treatment. When animals were subsequently provided with normal drinking water, intestinal re-colonization was observed one week later. The treatment with antibiotics does not render the gut sterile but rather substantially reduces the bacterial load and perhaps alters the composition of the normal gut microflora.

Oral antibacterial treatment also provoked morphological alterations in mice; splenic sizes were significantly reduced in treated mice (P<0.01) and significant increases in the size and weights of cecums (P<0.01) were observed when compared to naïve mice. Histological sections of the cecums showed no pathological signs. Increases of cecum sizes are weights have been described (Koopman, et al. (1986) *Lab. Anim.* 20:286-290). Bacterial re-colonization observed one week after the end of the antibiotics treatment was associated with partial restoration of body, spleen and cecum weights and sizes.

Mice were sacrificed on day 7 of antibiotic treatment and Peyer's Patches (PPs), mesenteric lymph nodes (MLNs), spleens and head and neck lymph nodes (HNLN) were aseptically removed and lymphocyte suspensions were prepared according to conventional methods. A control group of mice included treatment with the same antibiotics intraperitoneally (i.p.). $T_{reg}$ cells subsets were analyzed using fluorochrome-conjugated monoclonal antibodies specific for surface CD4 and CD25 antigens (R&D Systems, Minneapolis, Minn.). Intracellular staining for Foxp3 was accomplished using FITC-anti-Foxp3 monoclonal antibody (eBioscience, San Diego, Calif.). Bound fluorescence was analyzed with a FAC-SCANTO (BD Biosciences, Franklin Lakes, N.J.).

A major change in the GALT was observed, wherein a significant reduction (P<0.01) of $T_{reg}$ cells from the PP was evident but not the MLN of antibiotic-treated mice. Conversely, an increase in the $T_{reg}$ cell population was observed in the spleen (P<0.001) and cervical lymph nodes (P<0.001) following antibiotic treatment. Spleen and cervical nodes harvested from mice treated with antibiotics demonstrated a significant reduction in the percentage of CD25 expression in total $CD4^+$ T cells analyzed. This reduction was not observed in spleens and HNLN, where microflora-depleted animals presented a significantly enhanced population in $T_{reg}$ cells when compared to normal mice. However, FoxP3 expression in $CD4^+CD25^+$ T cells was significantly diminished in microflora-depleted animals, even in spleens and HNLN.

Retinoic acid was also detected in Peyer's Patches according to established methods. Briefly, a monolayer of retinoid reporter cell line was co-cultured with whole Peyers Patches overnight at 37° C. with 5% $CO_2$. After incubation, tissues were removed and cells were treated for 1 minute at 37° C. with FITC staining for gene reporter, and analyzed by FACS (Wagner (1997) supra). The results of this analysis indicated that the amount of retinoic acid detected in PPs of C57, treated with antibiotics against gut microflora, was reduced when compared to the levels observed in PPs of normal mice. These results indicate that a reduction of retinoic acid in microflora-depleted mice can influence the FoxP3 expression in $T_{reg}$ cells.

Splenic and HNLN lymphocytes were harvested from naïve and mice treated orally with antibiotics and cultured for 72 hours in the presence of anti-CD3 and anti-CD28 antibodies and supernatants were used to quantify the production of cytokines by LUMINEX. Results showed that immune responses of antibiotic-treated mice were modified, and splenic and HNLN lymphocytes produced different patterns of cytokines when compared to control naïve mice. Alteration of commensal populations produced a significant reduction of splenic IFN-γ, MIP-1α, MIP-1β, MCP-1, and IL-6, whereas IL-13 was significantly enhanced when compared to naïve levels.

To further analyze this reduction in cytokines, Peyer's Patches (PP), Mesenteric LN (MLN), Splenic and Cervical LN (CLN) lymphocytes were harvested from naïve mice (Table 1) and mice treated orally with antibiotics and co-stimulated with αCD3/αCD28 antibodies (Table 2). Results show that the reduction of gut commensal microflora significantly diminished the production of MIP-1α, MIP-1β and IL-6 in PP. Mesenteric lymph nodes of animals treated with antibiotics produced lesser amounts of IFN-γ, MIP-1α, MIP-1β and IL-6, and significantly increased levels of IL-13. Splenic and CLN cells derived from these mice produced reduced IFN-γ, MIP-1α, MIP-1β, MCP-1, IL-17 and IL-6 levels, whereas IL-13 and IL-10 in CLN were significantly enhanced when compared to untreated control mice. To study the cytokine pattern of mice treated with antibiotics and subsequently colonized with *B. fragilis* or ΔPSA *B. fragilis*, splenic lymphocytes were harvested from naïve and mice treated orally with antibiotics and stimulated ex vivo with αCD3/αCD28 antibodies. When treated mice were colonized with wild-type or ΔPSA *B. fragilis*, significant enhancements of IFN-γ and IL-10 production was observed. However, IL-10 production following reconstitution with ΔPSA *B. fragilis* was significantly lower than that observed following reconstitution with wild-type *B. fragilis*. ΔPSA *B. fragilis* colonization enhanced very significantly IL-6, as well as IL-17, whereas this increase was not seen following colonization with the wild-type bacteria expressing PSA. Interestingly, wild-type *B. fragilis* induced significant increases in the expression of the transcription factor GATA-3 and SMAD-3 when compared to ΔPSA.

TABLE 1

| Cytokine | Cytokine Concentration (pg/ml) | | | |
|---|---|---|---|---|
| | PP | MLN | SPL | CLN |
| IFN-γ | 311 ± 27 | 798 ± 150 | 3500 ± 110 | 2761 ± 110 |
| TNF-α | 11.2 ± 2 | 10.8 ± 2.0 | 67.3 ± 12 | 140 ± 64 |
| MIP-1α | 910 ± 270 | 1102 ± 112 | 4050 ± 270 | 3142 ± 310 |
| MIB-1β | 3510 ± 758 | 4220 ± 250 | 20853 ± 988 | 17045 ± 461 |
| MCP-1 | 381 ± 21 | 433 ± 151 | 1545 ± 230 | 2090 ± 152 |
| IL-6 | 619 ± 84 | 761 ± 78 | 1598 ± 120 | 1040 ± 430 |
| IL-17 | 131 ± 55 | 831 ± 150 | 820 ± 430 | 1642 ± 321 |
| IL-4 | 101 ± 20 | 110 ± 81 | 273 ± 103 | 216 ± 31 |
| IL-10 | 81 ± 11 | 320 ± 51 | 144 ± 41 | 252 ± 47 |
| IL-13 | 210 ± 27 | 185 ± 6.3 | 405 ± 99 | 322 ± 101 |

TABLE 2

| Cytokine | Cytokine Concentration (pg/ml) | | | |
|---|---|---|---|---|
| | PP | MLN | SPL | CLN |
| IFN-γ | 304 ± 78 | 380 ± 30* | 900 ± 430* | 2522 ± 310 |
| TNF-α | 14 ± 8.1 | 14.2 ± 3.0 | 43 ± 8.2 | 121 ± 13 |

TABLE 2-continued

| Cytokine | Cytokine Concentration (pg/ml) | | | |
|---|---|---|---|---|
| | PP | MLN | SPL | CLN |
| MIP-1α | 708 ± 70* | 818 ± 77± | 3100 ± 43* | 741 ± 28* |
| MIB-1β | 3040 ± 652* | 4177 ± 321 | 15120 ± 50* | 14230 ± 63* |
| MCP-1 | 334 ± 82 | 120 ± 30.2* | 110 ± 31* | 410 ± 411* |
| IL-6 | 434 ± 22* | 331 ± 21* | 99 ± 22* | 622 ± 73* |
| IL-17 | 110 ± 31 | 201 ± 20* | 265 ± 12* | 1121 ± 103* |
| IL-4 | 122 ± 77 | 131 ± 14 | 255 ± 41 | 210 ± 23 |
| IL-10 | 94 ± 8.2 | 313 ± 40 | 123 ± 24 | 391 ± 12* |
| IL-13 | 194 ± 42 | 731 ± 75* | 1130 ± 67* | 886 ± 118* |

*$P < 0.05$ for cytokine levels of naïve vs. antibiotic treated mice in each tissue analyzed.

Example 3

Oral Treatment with Antibiotics Alters Immune Cell Populations

Flow cytometry was used to compare the populations of T cells, B cells, dendritic cells (DC), macrophages, natural killer (NK) cells and NKT cells. A significant reduction in $CD4^+$ T cells and enhanced $CD8^+$ T cells response was observed in mice treated orally with antibiotics when compared to naïve and i.p. treated mice. Phenotypic analysis of the various immune compartments within the PP of animals treated orally with antibiotics showed a significant reduction in T, B and $CD11c^+CD11b^+$ DC percentages. Conversely, there was a significant increase in $CD11c^+CD11b^+$ DCs when compared to either naïve or mice treated i.p. with the same antibiotic cocktail. Percentages of $CD11b^+F4/80^+$ monocytes, NK and NKT cells of treated mice failed to show any significant difference when compared to untreated control mice. The MLN of mice treated with oral antibiotics showed a significant reduction in total T cells, but no change in B, $CD11b^+F4/80^+$ monocytes, NK, NKT or $CD11c^+CD11b^+$ or $CD11b^-$ DC populations. The percentage of splenic T cells was significantly higher in orally treated than naïve and i.p. treated mice. No alterations were observed in $CD11c^+CD11b^+$, $CD11c^+CD11b^-$ and $CD11c^+Gr-1^+$ DCs, $CD11b^+F4/80^+$ monocytes. A significant reduction in NK and NKT cell percentages in the spleen was observed in mice after oral treatment with antibiotics. Analysis of CLN showed that percentages of T cells were reduced significantly in mice treated orally with antibiotics, with no modifications in the rest of cellular populations compared.

Oral treatment with antibiotics altered significantly $CD4^+$ T cell subpopulations. FACS analysis revealed that the frequency of $CD4^+CD25^+$ T cells was reduced in PP of mice orally treated with antibiotics, but significantly increased ($P<0.01$) in MLN, spleens and CLN when compared to naïve and i.p. treated mice. Lymph nodes of treated mice showed reciprocal reduction and enhancement of activated $CD45Rb^{low}CD4^+$ T cells in MLN and CLN of $CD25^+$ T cell populations when compared to naïve and mice treated i.p. with antibiotics. FACS analysis showed that oral treatment with antibiotics provoked a significant reduction ($P<0.01$) in the frequency of $FoxP3^+CD25^+$/total $CD4^+$ T cells in spleens but otherwise unchanged from control values. When total numbers of $FoxP3^+T_{reg}$ cell were compared, significant reductions ($P<0.01$) were measured in PP and spleens of mice subjected to oral treatment with antibiotics. However, gut flora alterations enhanced $FoxP3^+T_{reg}$ cell numbers significantly ($P<0.01$) in MLN and CLN when compared to naïve and mice treated i.p. These results indicate that a combination of Th2-type immune responses and the induction of regulatory T cell subpopulations may provide an important framework that can offer protection against EAE when bacterial communities of the gut are challenged with antibiotics.

Alterations in $FoxP3^+$ $T_{reg}$ cells were further analyzed. It was determined whether the commensal Bacteroides and the presence of PSA in *B. fragilis* would affect the regulation of the immune system of these animals. SJL mice were colonized by gavage with *B. fragilis* or with ΔPSA *B. fragilis* on day 0 post antibiotic treatment and $T_{reg}$ cell populations were analyzed 3, 7 and 10 days gut post-colonization in PPs, MLNs, spleens or CLN. Mono-reconstitution with *Bacteroides* influenced the population of $T_{reg}$ cells in the gut-associated lymph nodes, spleen and CLN. FoxP3 expression levels in these $T_{reg}$ cells analyzed remained above 70%. Total numbers of $FoxP3^+T_{reg}$ cells were significantly enhanced in CLN of mice reconstituted with wild-type *B. fragilis* when compared to ΔPSA *B. fragilis* and control mice treated with antibiotics. Significant enhancement of $FoxP3^+T_{reg}$ cells in total $CD4^+$ T cells were seen in spleens and CLN of wild-type versus ΔPSA *B. fragilis* reconstituted mice. These results indicate that the presence of bacteria in the gut is associated with global immune homeostasis, not only within the GALT compartments but also in other peripheral immune sites, such as spleen and CLN.

Studies have demonstrated that CD39 (ENTPD1) mediates immune suppression of regulatory T cells by hydrolysis of ATP and AMP into adenosine monophosphate (5'AMP). CD39 is a 78 kDa GPI-anchored glycoprotein expressed on vascular endothelial cells, some T lymphocytes (particularly $T_{reg}$ cells), B cells, NK cells, NKT cell, dendritic cells, macrophages and monocytes. CD39+ $T_{reg}$ cells are known to be immunosuppressive, regulating Th17 proliferation (Fletcher, et al. (2009) *J. Immunol.* 183:7602-7610). These CD39+ $T_{reg}$ cells suppress the production of IL-17 in a cell-to-cell contact-dependent mechanism, independent of IL-10. Moreover, it has been suggested that ATP hydrolytic function of CD39+ $T_{reg}$ cells is impaired in multiple sclerosis patients. CD39 deficiency enhances proinflammation in the gut and experimental colitis in mice (Friedman, et al. (2009) *Proc. Natl. Acad. Sci. USA* 106:16788-93). This later study suggested that human inflammatory bowel disease (IBD) susceptibility might be exacerbated due to CD39 polymorphism. In this respect, it was determined whether PSA could enhance the frequencies of FoxP3+ $T_{reg}$ cells and induce the acquisition of a CD39+ phenotype in FoxP3+ $T_{reg}$ cells.

For this analysis, peripheral blood mononuclear cells (PBMCs) were obtained from healthy donors (n=6) or MS patients (n=6, with relapsing disease) and cryopreserved at −140° C. until used. Samples were thawed individually, resuspended in saline solution, and counted. Human PBMCs were cultured in AIM V medium supplemented with IL-2 (50 U/ml) and 2.5% human serum. Cells were plated in 96-well plates at 100,000 cells per plate with anti-CD3/anti-CD28 beads (Dynal). Cells were exposed to 50 micrograms/ml of a highly purified preparation of polysaccharide-A (PSA) obtained from the human gut commensal *B. fragilis*. Negative controls were cultured in the presence of plain media. In some experiments, PSA treatment was combined with retinoic acid (RA; 4 nM), with transforming growth factor-beta (TGF-β; 5 ng/ml), or with RA plus TGF-β. RA alone, TGF-β alone and RA plus TGF-β, were used as positive controls. After 5 days of culture, the acquisition of a regulatory phenotype (FoxP3+) and CD39 expression was compared by flow cytometry. Supernatants of the cell cultures were collected and stored at −80° C. until used. Culture supernatants were used to compare IL-10 levels. For interleukin 10 (IL-10) detection, a commercially available IL-10-specific ELISA (BioLegend) was used.

It has been demonstrated that human naïve CD4+ T effector cells can be converted to adaptive FoxP3+CD4+ T regulatory cells in vitro (Kasper, et al. (2009) *Multiple Sclerosis* 15:S5-277). The results of the present analysis indicated that the addition of PSA to PBMC cultures enhanced the acquisition of FoxP3 by CD4+ T cells when compared to cells cultured without PSA. TGF-β had an additive effect with PSA in the production of FoxP3+ $T_{reg}$ cells, but not when used alone. Retinoic acid had no effect in the enhanced FoxP3+ phenotype acquisition. CD39+ $T_{reg}$ cells have shown to be immunosuppressive, regulating the Th17 proliferation (Fletcher, et al. (2009) supra). Therefore, the frequency of CD39 expression in FoxP3+ and FoxP3− CD4+ T cells was compared in human PBMCs. PSA enhanced the expression of CD39+ in FoxP3+, but not in FoxP3−CD4+ T cells when compared to cells cultured without PSA. Moreover, wherein PSA plus TGF-β exacerbated the expression of CD39 in FoxP3+ $T_{reg}$ cells, the addition of retinoic acid to PSA further enhanced the expression of CD39+ in FoxP3+ $T_{reg}$ cells as compared to PSA alone. The enhanced acquisition of CD39+phenotype of $T_{reg}$ cells after stimulation with PSA or PSA and retinoic acid is of interest since both molecules are found in the GALT and are both considered immunoregulatory.

Figure 7A:
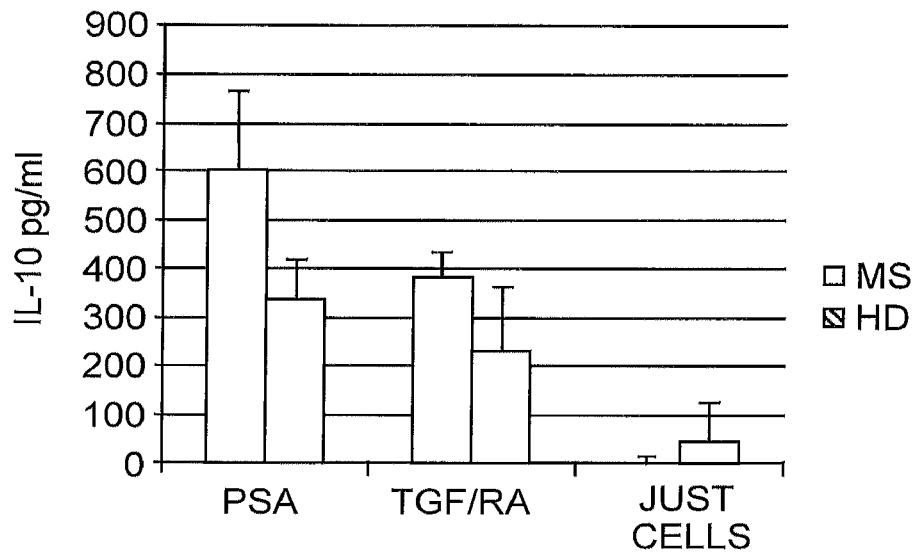
FIG. 7A shows interleukin (IL)-10 production by relapsing remitting multiple sclerosis (MS, n=6) patient and healthy donor (HD, n=6) peripheral blood mononuclear cells (PBMCs) treated with PSA or TGF-β/retinoic acid.
Figure 7B:
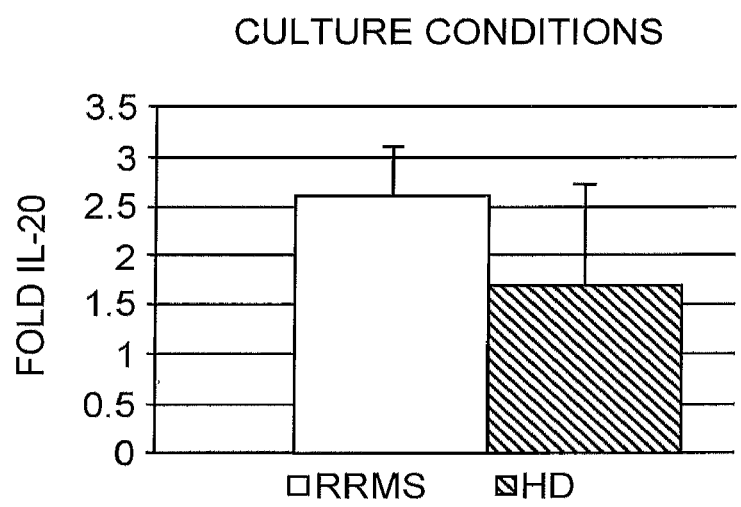
FIG. 7B shows the fold difference in IL-10 production between PSA and non-PSA stimulated PBMCs from relapsing remitting multiple sclerosis (RRMS, n=6) patients and healthy donors (HD, n=6).

IL-10 production by human PBMC from healthy donors and MS patients was also analyzed after stimulation with purified PSA. This analysis indicated that there was a substantial increase in IL-10 production by the MS patient PBMC in response to in vitro stimulation with PSA as compared to the combination of RA plus TGF-β (FIG. 7A). Moreover, these results demonstrated that PSA enhances IL-10 production in MS patients to a greater extent than in healthy donors (FIG. 7B).

Example 4

Microflora-Mediated Protection Against EAE

In order to ascertain whether the alterations of the immune responses to modifications of gut commensal composition would alter the peripheral immune responses and global homeostasis, EAE was induced with $PLP_{139-151}$ in naïve and SJL mice previously treated with antibiotics (FIG. 1). Control mice were treated with PBS and i.p. with the same antibiotics. There have been different reports implicating a direct neurological effect by injections of minocycline, a $2^{nd}$ generation type of tetracycline. Minocycline provides partial protection against EAE when combined with glatiramer acetate or IFN-β (Ruggieri, et al. (2008) *J. Neuroimmunol.* 197:140-146; Giuliani, et al. (2005) *J. Neuroimmunol.* 165:83-91) provoking a down-regulation in the antigen presentation capability of blood monocyte-derived DCs antigen presentation in mice and activation capability in MS patients (Ruggieri, et al. (2008) supra). FIG. 1 and Table 3 show that oral treatment with antibiotics previous to challenge with PLP reduced significantly the severity of EAE when compared to PBS control and i.p. treated animals.

TABLE 3

| Treatment[a] | Onset[b] | Mortality (%) | Cumulative Score[c] |
|---|---|---|---|
| PBS-rat IgG | 10.1 ± 0.5 | 37.5 | 56.2 ± 0.2 |
| PBS-aCD25 | 9.0 ± 0.7* | 75* | 95.2 ± 1.1* |
| Oral Treated-rat IgG | 11.7 ± 0.5 | 0 | 6 ± 0.1 |
| Oral Treated-aCD25 | 9.5 ± 0.4* | 25*,[T] | 47.7 ± 0.5*,[T] |
| i.p. Treated-rat IgG | 10.2 ± 0.7 | 50 | 70.1 ± 1.1 |
| i.p. Treated-aCD25 | 9.2 ± 0.7* | 75* | 97.5 ± 1.2* |

[a]SJL Mice were treated orally or i.p. with antibiotics and subsequently with 300 mg of rat IgG or anti-CD25 mAb on days 3 and 5. On day 7, mice were challenged s.c. with 200 mg $PLP_{139-151}$ in complete Freund's adjuvant and 200 ng PT i.p. (days 0 and 2 post-EAE induction);
[b]Mean day ± SEM of clinical disease onset;
[c]Cumulative clinical scores were calculated as the sum of all clinical scores from disease onset after day 25 post-challenge, divided by the number of mice in each group.
*p < 0.001 for PBS vs oral t and oral vs i.p. treatment, and oral vs i.p. treatment.
*P < 0.05 for rat IgG vs aCD25 treated among groups (PBS, oral or i.p. treated with antibiotics).
[T]P < 0.01 for oral treated-aCD25 vs PBS-aCD25 and i.p. treated-aCD25.

Whereas all PBS- and i.p.-treated mice developed clinical scores (12/12) with maximum scores 5, incidence in animals treated with antibiotics was lower (8/12) and showed maximum clinical scores 3. Significant differences were observed in the onset of the disease and the cumulative scores of PBS vs. i.p. vs. orally treated mice. Demyelination and nucleated cell infiltration levels were reduced in orally treated mice. No significant differences were observed between PBS- and IP-treated mice (Table 4). Moreover, no significant differences in bacterial counts, body, or splenic weights were observed in mice treated i.p. with antibiotics when compared to naïve mice, indicating that the protection observed was due to the modification of bacterial populations in the gut.

TABLE 4

| Treatment[a] | Onset[b] | Cumulative Score[c] | Demyelination[d] | Infiltration[e] |
|---|---|---|---|---|
| PBS | 8.6 ± 0.2 | 57.6 ± 0.2 | 2.0 ± 0.3 | 3.5 ± 0.2 |
| Oral | 10.7 ± 0.5*,* | 7.6 ± 1.1*,* | 0.7 ± 0.2*,* | 0.8 ± 0.4*,* |
| i.p. | 8.2 ± 0.2 | 48.4 ± 1.7 | 2.8 ± 0.5 | 3.2 ± 0.7 |

[a]SJL were challenged s.c. with 200 mg $PLP_{139-151}$ in complete Freund's adjuvant and 200 ng PT i.p. on days 0 and 2. Mice were treated orally or i.p. with antibiotics or PBS for 7 days prior EAE induction;
[b]Mean day ± SEM of clinical disease onset;
[c]Cumulative clinical scores were calculated as the sum of all clinical scores from disease onset after day 25 post-challenge, divided by the number of mice in each group.
*p < 0.001 for PBS vs oral t and oral vs i.p. treatment;
[d]Mean score ± SEM of demyelination: of spinal cords was scored from 0 to 4 in each mouse separately, and the mean score ± SEM was calculated.
*p < 0.001 for PBS vs oral t and oral vs i.p. treatment;
[e]Mean score ± SEM of inflammation: the infiltration of nucleated cells into spinal cords was scored from 0 to 4 in each mouse separately, and the mean score and SEM were calculated.
*p < 0.001 for PBS vs oral t and oral vs i.p. treatment.

When mice were treated with the antibiotics during the entire length of the experiment, mice were fully protected with no evidence of disease development as determined by clinical score. These data indicate that intestinal colonization with certain bacterial population can evoke clinical disease consistent with EAE.

PCR analysis showed enhanced levels of IL-13 expression in the brains of animals protected against EAE by oral treatment with antibiotics when compared to PBS treated mice and animals treated i.p. with antibiotics. No significant differences in IL-13 production were observed in brains of mice treated i.p. and control PBS-treated mice.

Example 5

Wild-Type *B. fragilis*-Converted FoxP3$^+$T$_{reg}$ Cells Confer Prophylactic and Therapeutic Protection Against EAE Flow cytometry analysis of the lymph nodes show that reconstitution of the gut with *B. fragilis* drives the enhancement of T$_{reg}$ cell populations. Thus, it was determined whether reconstitution with wild-type or ΔPSA *B. fragilis* could determine the conversion rates of CD4$^+$CD25$^-$ T$_{effector}$ cells into FoxP3$^+$T$_{reg}$ cells in the MLN. CD4$^+$CD25$^-$ T cells isolated from MLN of naïve mice treated with antibiotics, and mice treated with antibiotics and subsequently reconstituted with wild-type or ΔPSA *B. fragilis* were cultured in vitro for 4 days in the presence of IL-2 and increasing concentrations of TGF-β and retinoic acid. Highest T$_{reg}$ cell conversion levels of naïve CD25$^-$T cells were obtained at retinoic acid concentrations of 2 and 4 nM (not significant differences) and 0.5 and 5 ng/ml of TGF-β (not significant differences). When no additional retinoic acid was included in the cultured media, CD25$^-$T cells sorted from MLN of mice reconstituted with wild-type *B. fragilis* had significant enhanced levels of conversion into T$_{reg}$ cells when compared to the rest of the experimental groups. Significant increases in the conversion rates of wild-type *B. fragilis* CD25-T cells were still observed at retinoic acid concentrations of 2 nM (0.5 and 5 ng/ml of TGF-β). Conversion rates were significantly enhanced in all groups when TGF-β concentrations were approaching the optimal concentration (Niess, et al. (2008) *J. Immunol.* 180: 559-68) independently of retinoic acid levels.

Figure 2:
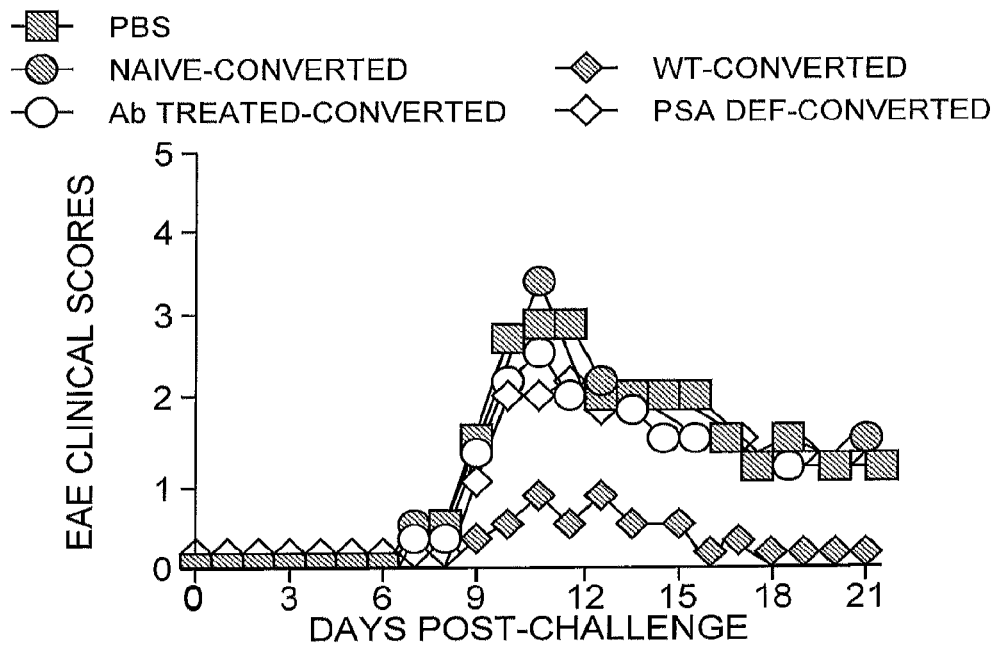
FIG. 2 shows that adoptive transfer of converted cells from CD4$^+$ T cells of animals reconstituted with wild-type *B. fragilis* protected against subsequent EAE induction whereas converted cells from naïve, antibiotics-treated, or PSA *B. fragilis* reconstituted mice did not confer any protection against the disease. *, P<0.01, represents statistical differences between groups.

These results show an enhanced capacity of conversion to FoxP3$^+$T$_{reg}$ cells by CD25$^-$T cells purified from MLN of mice reconstituted with wild-type *B. fragilis* when cells were cultured in the presence of IL-2, 0.5 or 5 ng/ml but no retinoic acid. Based on the significant differences in the conversion rate observed, the capacity of these converted FoxP3$^+$T$_{reg}$ cells to protect the development of EAE after adoptive transfer was determined. Cells cultured in 5 ng/ml of TGF-β and no retinoic acid were collected after 4 days and adoptively transferred. The results of this analysis showed that cells converted from CD4+ T cells of animals reconstituted with wild-type *B. fragilis* protected against subsequent EAE induction whereas converted cells from naïve, antibiotic-treated, or ΔPSA *B. fragilis* reconstituted mice did not confer any protection against the disease (FIG. 2).

Figure 4:
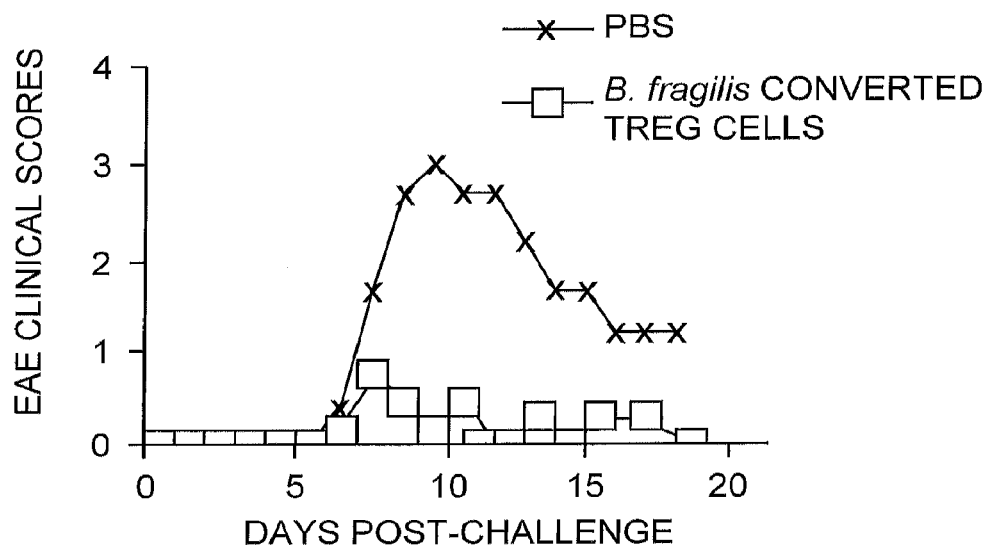
FIG. 4 shows therapeutic adoptive transfer of regulatory T cells provides protection against EAE. Naïve CD4+ T cells from mice treated with antibiotics and subsequently colonized with B. fragilis showed enhanced rates of conversion into $T_{reg}$ cells. FoxP3+ converted cells were sorted and adoptively transferred (1×10⁶ cells/mouse) into naïve recipient mice four days after EAE was induced.

When *B. fragilis* converted T$_{reg}$ cells were adoptively transferred into naïve mice 4 days after EAE induction, a significant reduction in the EAE clinical scores average was observed. These results indicate a therapeutic effect of converted T$_{reg}$ cells of mice reconstituted with PSA-producing *B. fragilis* (FIG. 4).

Example 6

Regulatory T Cells Induced by Wild-Type *B. fragilis* are Critical for Protection Against EAE To elucidate the potential role of regulatory T cells induced in vivo by reconstitution with wild-type or ΔPSA *B. fragilis* in the protection observed against EAE, adoptive transfer experiments were conducted. In the first experiment, the protective role of CD4$^+$ or CD8$^+$ T cells was compared. SJL mice were treated for seven days with ampicillin, vancomycin, neomycin sulfate and metronidazole dissolved in drinking water, or with normal drinking water (naïve control group). After the treatment, CLN were harvested and CD4$^+$ or CD8$^+$ T cell populations were enriched by selection with magnetic microbeads. Adoptive transfer of 1×10$^6$ cells/mouse (≥96% pure) was performed 1 day prior to EAE induction with PLP$_{139-151}$. CD4$^+$ T cells isolated from CLN of mice treated with antibiotics significantly reduced the EAE clinical scores of SJL mice when compared to CD4$^+$ T cells obtained from naïve mice. By contrast, no significant differences were observed in the clinical outcome of the disease after adoptive transfer of CD8$^+$ T cell-enriched population from CLN of mice treated with antibiotics when compared to PBS treated mice or mice treated with naïve CD8$^+$ T cells. These results indicate that CD8$^+$ T cell of mice treated with antibiotics do not play a role in the protection against EAE observed previously.

It was next determined whether CD25$^+$CD4$^+$ or CD25$^-$CD4$^+$ T cells obtained from CLN of mice treated with antibiotics would be suppressive in vitro and would confer protection against EAE after adoptive transfer. The suppressive capacity of antibiotics treated FoxP3-enriched CD25$^+$CD4$^+$ T cells was significantly enhanced at 1:10 T$_{supp}$:T$_{effector}$ ratio. Despite the statistical significance at one single cell ratio, it is possible that the observation might have no biological relevance. In order to analyze a potential protective role of these cell populations, naïve recipient SJL mice were adoptively transferred with 4×10$^5$ cells/mouse of CD25$^+$CD4$^+$ or CD25$^-$CD4$^+$T cells obtained from CLN of naïve or mice previously treated with antibiotics one day prior EAE induction with PLP$_{139-151}$. When CD25$^+$CD4$^+$ T cells (>75% FoxP3$^+$) purified from CLN of SJL mice treated with antibiotics a significant reduction of the EAE clinical scores was observed. No protection was observed after adoptive transfer of the control arms including CD25$^+$CD4$^+$T cells purified from mice treated with antibiotics, CD25$^+$CD4$^+$ and CD25$^-$CD4$^+$ T cells obtained from naïve mice.

Analysis of the cytokine profile of adoptively transferred CD25$^+$CD4$^+$ and CD25-CD4+T cells showed that protective CD4$^+$CD25$^+$ T cells (>75% FoxP3$^+$) sorted from mice treated orally with antibiotics produced significantly enhanced levels of IL-10 (P<0.01) and IL-13 (not significant) when compared to naïve CD4$^+$CD25$^+$ T cells. When CD25$^-$CD4$^+$T cells were compared, those obtained from oral-treated treated mice showed significant reductions in IFN-γ and IL-17, and no significant differences in IL-10 and IL-13 when compared to naïve levels.

To confirm the protective capacity of the T$_{reg}$ cells from oral antibiotic treated mice, in vivo neutralization of CD25-expressing cells was performed using a depleting anti-CD25 mAb (clone PC-61). Two doses of 300 μg/mouse on days 3 and 5 after the initiation of oral antibiotic treatment reduced the CD25$^+$ in CD4$^+$ T cells of naïve mice as well as mice treated with either oral or i.p. with antibiotics when compared to control treatment with rat IgG isotype control. Partial reversion of protection was observed by depletion of CD25$^+$ T cells in mice treated with oral antibiotics. The onset of clinical disease occurred earlier ($P<0.05$) in all groups treated with anti-CD25 mAb when compared to rat IgG treated mice (Table 3). The cumulative scores and mortality of mice treated orally with antibiotics and subsequently with anti-CD25 mAb were significantly more severe ($P<0.05$) when compared to mice treated orally with antibiotics and injected with rat IgG (Table 3). EAE clinical scores were also significantly reduced in CD25-neutralized mice previously treated with antibiotics when compared to either naïve ($P<0.05$) or i.p. treated ($P<0.05$) mice.

Figure 3:
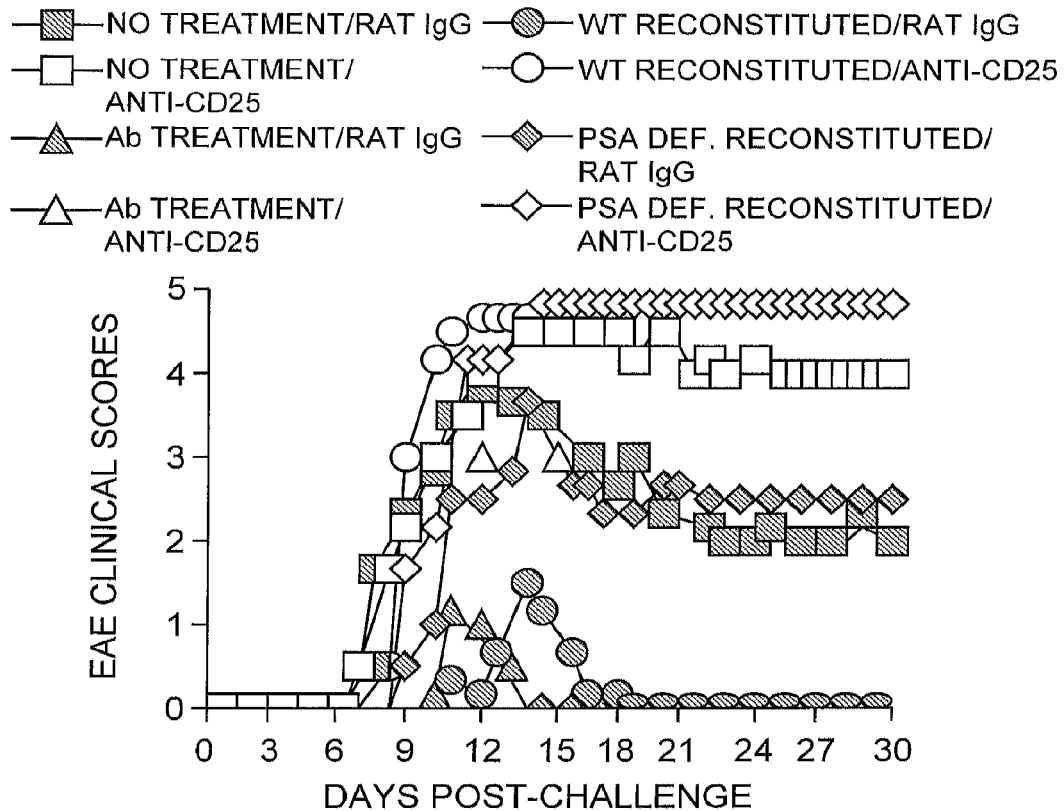
FIG. 3 shows that CD25$^+$CD4$^+$ T cells from wild-type *B. fragilis* reconstituted mice confer protection against EAE. CLN of mice treated with antibiotics and subsequently reconstituted with wild-type (WT) or ΔPSA *B. fragilis* were harvested and CD4+CD25− (FoxP3+≈10%) and CD4+CD25+ T cells (FoxP3+≥75%) were sorted by FACS and adoptively transferred (4×10⁵ cells/mouse) into naïve recipient SJL mice. One day after adoptive transfer, mice were EAE induced with $PLP_{139-151}$. Treatment with anti-CD25 MAb reduced very significantly the CD25+ percentages in CD4+ T cells of naïve, Ab-treated and reconstituted mice when compared to treatment with rat IgG isotype control. When EAE was induced, protection observed in mice treated with antibiotics and reconstituted with WT B. fragilis was lost. Depicted are the combined results from two separate experiments for a total of 8 mice/group: *, P<0.01 for naïve vs. oral treatment and oral vs. i.p. treated mice.

To further analyze adoptive transfer, CLN of mice treated with antibiotics and subsequently reconstituted with wild-type or ΔPSA $B.$ $fragilis$ were harvested seven days after bacterial reconstitution. $CD4^+CD25^-$ ($FoxP3^+\approx10\%$) and $CD4^+CD25^+$ T cells ($FoxP3^+\geq75\%$) adoptively transferred ($4\times10^5$ cells/mouse) into naïve recipient SJL mice. One day after adoptive transfer, mice were EAE induced with $PLP_{139-151}$. The results showed that adoptive transfer of $CD4^+CD25^+$ T cells from CLN of mice treated with antibiotics, and from mice reconstituted with wild-type $B.$ $fragilis$ reduced significantly the EAE clinical scores when compared to PBS control mice (FIG. 3). When $CD4^+CD25^+$ T cells of ΔPSA $B.$ $fragilis$ reconstituted mice were transferred, a reduced level of protection was observed. No protection was conferred by adoptively transferred $CD4^+CD25^-$ T cells from CLN of mice treated with antibiotics, or from mice reconstituted with ΔPSA $B.$ $fragilis$. By contrast, a partial reduction of EAE clinical scores was observed when $CD4^+CD25^-$ T cells from wild-type $B.$ $fragilis$ reconstituted cells were transferred.

In vivo experiments of CD25 depletion were performed in order to confirm their critical role in the control of EAE development. Mice subjected to treatment with antibiotics and bacterial reconstitutions were treated i.p. with two doses of anti-CD25 mAb (PC61) before EAE induction. Antibody treatment reduced significantly the $CD25^+$ T cell populations in lymph nodes and whole blood samples in all groups.

These results indicate that the EAE protection observed in mice reconstituted with wild-type $B.$ $fragilis$ could be driven by different suppressive populations of $CD4^+CD25^-$ and $CD25^+$ T cells. This observation indicates that gut commensal bacteria play an important role in the regulation of CNS demyelination and this regulatory effect can be under the control of specific bacterial antigens such as the capsular polysaccharide A antigen of the human commensal $B.$ $fragilis$.

Example 7

PSA-Producing $Bacteroides$ $fragilis$ Impair EAE Development in SJL Mice

Alterations in the immune profile in germ-free mice demonstrates a default Th2 bias and a significant reduction in proinflammatory IL-17-producing $CD4^+$ T cells compared to mice with an intact communal gut bacterial profile (Niess, et al. (2008) $J.$ $Immunol.$ 180:559). SJL mice were treated with antibiotics to deplete gut microbiota. To ascertain whether colonization with $B.$ $fragilis$ could influence the development of experimental autoimmune encephalomyelitis, the protective effect of wild-type and PSA-deficient $B.$ $fragilis$ against CNS autoimmune disorders was assessed. Antibiotic treated SJL mice were colonized with $10^{10}$ CFU/mouse of wild-type $B.$ $fragilis$ and ΔPSA $B.$ $fragilis$ and EAE was induced with autoreactive $PLP_{139-151}$ following standard procedures one week after bacterial reconstitution. Oral treatment with antibiotics reduced significantly the severity of EAE clinical symptoms after induction with $PLP_{139-151}$ (FIG. 1). Subsequent colonization with wild-type $B.$ $fragilis$ of mice with diminished microflora maintained the reduced EAE susceptibility. While clinical onset for normal SJL mice followed the expected EAE clinical outcome, mice treated with antibiotics and colonized with wild-type $B.$ $fragilis$ were resistant to the development of EAE, whereas the colonization of mice with ΔPSA $B.$ $fragilis$ rendered the mice susceptible to disease development. No protection was observed when naïve mice were colonized with $B.$ $fragilis$ or ΔPSA $B.$ $fragilis$.

To demonstrate the role of PSA in protection against EAE, mice were treated orally with 50 μg of purified PSA every other three days after EAE induction. Results showed a significant reduction in the EAE clinical scores in mice treated with purified PSA.

It has been demonstrated that $CD4^+$ T cell activation by PSA is dependent on the presentation of the antigen by $CD11c^+$ dendritic cells (Duan, et al. (2008) $Proc.$ $Natl.$ $Acad.$ $Sci.$ $USA$ 105:5183-8). After oral treatment of mice with fluorescence-labeled PSA, the polysaccharide is associated with $CD11c^+$ dendritic cells (DCs), but not $CD4^+$ T cells or $CD19^+$ B cells, in the mesenteric lymph nodes (MLNs), suggesting that DCs sample PSA from the intestine and migrate to the MLNs to initiate an immune response. The role of $CD11c^{high}CD103^+$ DCs in the conversion of naïve $CD4^+$ T cells into $Foxp3^+T_{reg}$ cells has been demonstrated (Coombes, et al. (2007) $J.$ $Exp.$ $Med.$ 204:1757-64).

In the present analysis, it was determined whether MLN $CD11c^{high}CD103^+$ DCs in the presence of anti-inflammatory environment could play a role inducing $T_{reg}$ cell differentiation in mice immunized with PSA of $B.$ $fragilis$. FACS analysis showed that the treatment with PSA significantly enhanced the percentages of these $CD11c^{high}CD103^+$ DCs. These observations indicate that $CD11c^{high}CD103^+$ DCs are involved in the regulation exhibited by exposure to PSA antigen.

Example 8

Figure 5A:
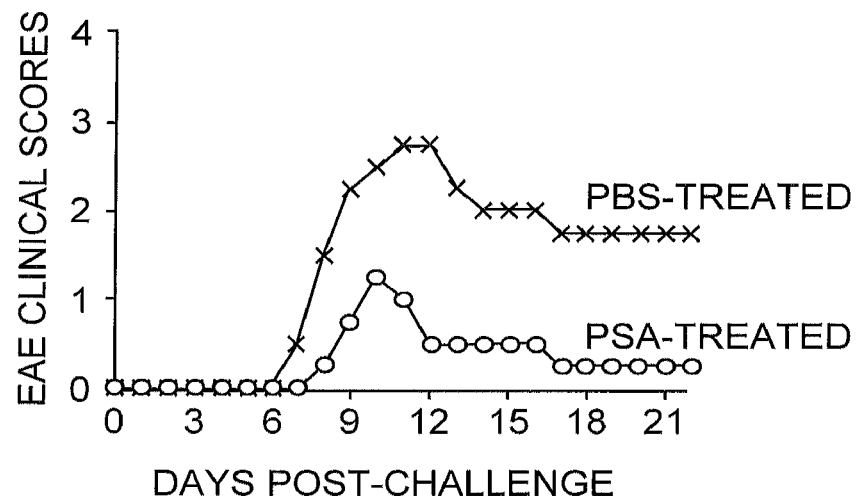
FIG. 5 shows that oral prophylactic treatment with purified PSA protects SJL and C57BL/6 mice against EAE. SJL (FIG. 5A) and C57BL/6 (FIG. 5B) mice were immunized with 100 µg of purified PSA by oral gavage every three days. Treatment was initiated 6 days prior EAE induction (with $PLP_{139-151}$ for SJL/J and $MOG_{35-55}$ for C57BL/6 mice) and terminated 9 days after disease induction. Depicted are the combined results of three independent experiments for a total of 12 mice/group.
Figure 5B:
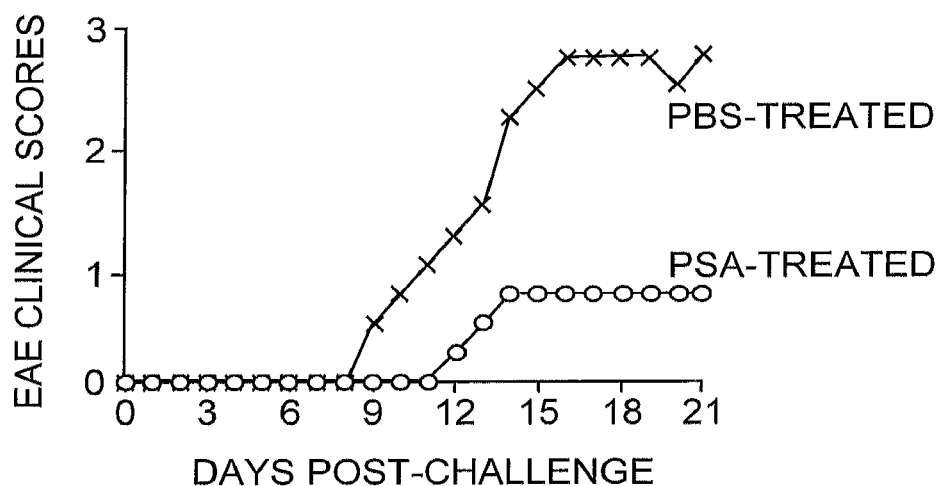

Oral Prophylactic and Therapeutic Treatment with Purified PSA Protect Mice Against EAE The results herein demonstrate that the absence of PSA in $B.$ $fragilis$ used to recolonize the intestinal track of mice restores susceptibility to EAE. The clinical implications of these observations support an important role for commensal bacterial antigen(s) in regulating peripheral immune homeostasis. Modulation of gut microflora represents a unique approach to control disease pathogenesis and offers an important pathway for the treatment of multiple sclerosis and perhaps other autoimmune conditions. Thus, the protective role of purified PSA against EAE was determined. Highly purified PSA, shown to confer protection against experimental colitis (Mazmnian, et al. (2008) $Nature$ 453:620-625) was obtained. Naïve SJL/J and C57BL/6 mice were treated orally with 100 μg of PSA every three days, starting 6 days before EAE induction with $PLP_{139-151}$ or $MOG_{35-55}$, respectively (FIG. 5). Treatment with purified PSA delayed the EAE clinical outcome and reduced the severity of the diseases in both strains of mice when compared to untreated (PBS group) mice.

Transversal sections of spinal cords of mice treated with either PSA or PBS were obtained 19 days after the induction of EAE. Spinal cord sections of mice treated with purified PSA showed a reduced demyelination and nucleated cell infiltration when compared to PBS-treated mice, in concordance to the reduced severity of the disease observed in the FIG. 5. Splenocytes of mice treated with PBS or PSA and subsequent induction of EAE were cultured in the presence of anti-CD3/anti-CD28 antibodies, purified PSA, $MOG_{35-55}$ or media. Supernatants were harvested after 48 hours and specific ELISA were used to quantify IFN-γ, IL-17, IL-10 and IL-13. Splenocytes obtained from mice treated with purified PSA and stimulated with anti-CD3/anti-CD28 antibody or with $MOG_{35-55}$ produced significantly lower levels of proinflammatory IFN-γ and IL-17 when compared to splenocytes of PBS-Treated mice. Cells from PSA-Treated mice cultured in the same conditions produced enhanced IL-13 and IL-10 when compared to mice treated with PBS. These results indicate that the treatment of mice with PSA induced a switch in the cytokine profile of the mice challenged with EAE, from a pathogenic Th17/Th1 to an anti-inflammatory or regulatory phenotype, which could in part explain the observed protection. Of interest, only IL-10 was produced by cells stimulated with purified PSA and, although IL-10 was produced by cells from both PBS- and PSA-Treated mice, a significant enhanced production was observed in mice treated with PSA.

Figure 6:
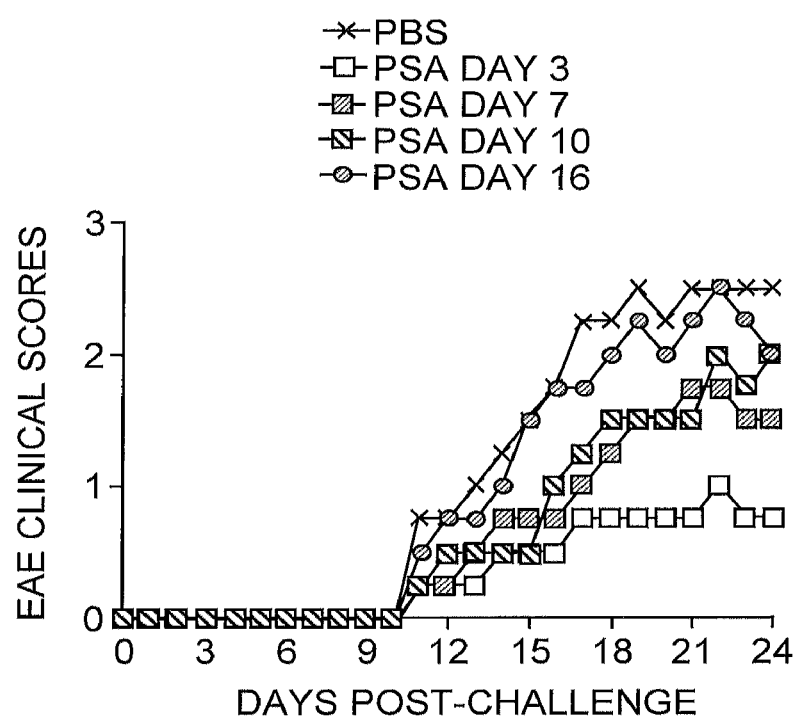
FIG. 6 shows that oral therapeutic treatment with purified PSA protects C57BL/6 mice against EAE. EAE was induced in C57BL/6 mice with $MOG_{35-55}$ on day 0. Independent groups of mice were treated with 100 µg of purified PSA by oral gavages every three days, starting at days 3, 7, 10 or after EAE induction. Depicted are the results of two independent experiments for a total of 8 mice/group.

The therapeutic effect of oral treatments with purified PSA was subsequently determined. EAE was induced in C57BL/6 mice and treatments with 100 μg of PSA were initiated 3, 7, 10 or 16 days after challenge with $MOG_{35-55}$. PSA was administered by oral gavages every three days (FIG. 6). Results showed that treatment 16 days after the induction of the disease did not confer any protection. When the treatment started on days 10 or 7 post-EAE induction, a reduction in the cumulative scores was observed when compared to control (PBS) mice and mice treated on day 16. When mice were treated on day 3 after EAE induction, a significant reduction in the EAE cumulative scores and severity when compared to PBS-Treated mice and those treated 16 days post-EAE induction. These reductions were also significant when compared to those observed in mice treated on days 7 or 10 after EAE induction (FIG. 6).

A significant reduction in the severity of EAE of SJL/J and C57BL/6 mice was observed when treated orally with PSA. Protection was observed when mice are treated before and after EAE induction. These studies were limited to one dosage strategy (100 μg of PSA every three days by oral gavages). These results indicate that the level of protection conferred could be improved by either an increased dose or frequency with PSA. Indeed, the "commensal" nature of the purified antigen provides a strategy for frequent administration while avoiding possible toxic side effects due to increased administration that has been associated with other FDA-approved and novel therapeutics currently under clinical trials for Relapsing/Remitting Multiple Sclerosis.

Example 9

Oral Treatment with Purified PSA Enhances CD103+ Dendritic Cells in EAE Mice

The role of $CD11c^{high}CD103^+$ dendritic cells in the conversion of naïve CD4+ T cells into $Foxp3^+T_{reg}$ cells has been demonstrated (Coombes, et al. (2007) *J. Exp. Med.* 204:1757-1764), and potential role for commensal bacteria in this conversion has been suggested (Coombes, et al. (2007) supra; Coombes & Powrie (2008) *Nat. Rev. Immunol.* 8:435-446). CD103+ DCs have been suggested to migrate from the intestine to the MLN, where they could generate $T_{reg}$ cells (Johansson-Lindbom, et al. (2005) *J. Exp. Med.* 202:1063-1073). Therefore, the percentages of CD103− and CD103+ CD11c− dendritic cells were compared in Peyer's Patches, spleens, mesenteric lymph nodes (MLN) and cervical lymph nodes (CLN) of EAE-induced or control mice treated orally with PSA or PBS.

Oral treatment against EAE with purified PSA significantly enhanced the percentages of CD103−CD11c+ dendritic cells in Peyer's Patches, and mesenteric and cervical lymph nodes. Moreover, a significant six- to seven-fold increase of CD103+CD11c+ dendritic cells was observed in mesenteric and mesenteric lymph nodes of mice treated with PSA when compared to untreated mice. Of particular interest was the observation that oral treatment of naïve, non-EAE mice with purified PSA significantly increased the percentages of CD103+CD11c+ dendritic cells in mesenteric lymph nodes, but not in the cervical lymph nodes. These results indicate that exposure to EAE antigens may be critical in the trafficking and migration of the CD103+ dendritic cells to the CNS and closely associated lymphoid tissue.

A critical role of $T_{reg}$ cells in the protection conferred by reconstitution with PSA-producing *B. fragilis* has been demonstrated. Recolonization of mice with reduced microflora by treatment with antibiotics with either wild-type or PSA-deficient *B. fragilis* enhances the percentages and numbers of $Foxp3^+T_{reg}$ cells. However, only the adoptive transfer of $T_{reg}$ cells purified from mice recolonized with PSA-producing *B. fragilis* confers protection against EAE. Cytokine analysis revealed that these protective cells produced enhanced levels of TGF-β and particularly IL-10. In vivo depletion of CD25+ cells confirmed the critical role of $T_{reg}$ cells in the protection conferred by PSA-producing *B. fragilis*. The percentages of $FoxP3^+T_{reg}$ cells were compared in EAE mice treated orally with PSA or PBS at the peak of the disease. Oral treatment with PSA enhanced $FoxP3^+T_{reg}$ cell percentages in spleens, and mesenteric and cervical lymph nodes when compared to PBS-Treated mice.

The results herein indicated that CD103+ dendritic cells were up-regulated when EAE mice were treated with purified PSA. Therefore, the effect of oral immunizations of naïve C57BL/6 mice with PSA was determined. The results of this analysis indicated that only mesenteric lymph nodes of mice treated with PSA had enhanced percentages of these cells when compared to PBS-immunized mice. No significant differences were observed in Peyer's Patches, spleens or cervical lymph nodes of mice after immunization with either PSA or PBS. Oral treatment of naïve C57BL/6 mice with PSA enhanced $FoxP3^+T_{reg}$ cell numbers in mesenteric lymph nodes and spleens, but not in the cervical lymph nodes. Oral immunizations with purified PSA enhanced the percentages of CD103+ dendritic cells and $T_{reg}$ cells in the mesenteric lymph nodes. $T_{reg}$ cells were also enhanced in spleens of PSA-immunized mice. When the same populations were compared in EAE mice, a significant increase in CD103+ dendritic cells and $T_{reg}$ cells was observed in spleens, and mesenteric and cervical lymph nodes of mice treated with PSA (and protected against the disease). The increases in the CD103+ dendritic cell populations in the cervical lymph nodes of PSA-Treated mice was particularly apparent, and indicated a possible migration of these mucosal-specific dendritic cells populations to peripheral lymphoid tissues that drain to the CNS. These accumulations were not observed in mice that were not subjected to EAE challenge.

Example 10

Food Products Containing Isolated *B. fragilis* PSA

Food products, foodstuffs or functional foods can be prepared by conventional procedures containing isolated, and optionally purified, *B. fragilis* PSA in an amount of 10 mg to 1000 mg per serving. Examples of such foods are soft drinks, bread, cookies, yogurt, ice cream, and sweets.

By way of illustration, an orange-Lemon juice drink, containing 10% juice and isolated *B. fragilis* PSA is prepared from the ingredients listed in Table 5.

TABLE 5

| Ingredients | [g] |
| --- | --- |
| Sugar syrup | 156.2 |
| Sodium benzoate | 0.2 |
| Ascorbic acid, fine powder | 0.2 |
| Citric acid 50% w/w | 5.0 |
| Pectin solution 2% w/w | 10.0 |
| Isolated *B. fragilis* PSA | 0.1 |
| Juice compound | 30.0 |
| (Orange juice concentrate | (483.3 |
| Lemon juice concentrate | 173.3 |
| Oily orange flavor | 5.0 |
| β-Carotene* | 10.0 |
| Deionized water) | 328.4) |
| Water to | 250.0 |

*10% Carotene working solution

The juice drink is prepared by dissolving sodium benzoate in water and, while stirring, add sugar syrup, ascorbic acid, citric acid, pectin solution, juice compound, and 150 mg of isolated *B. fragilis* PSA, one after the other. The bottling syrup is then diluted with (carbonated) water to one liter of beverage.

As a further illustrative example, a yogurt (typical serving, 225 g) containing 10 mg to 1000 mg per serving isolated *B. fragilis* PSA is prepared from the ingredients listed in Table 6.

TABLE 6

| Ingredients | [%] |
| --- | --- |
| Full fat milk (3.8% fat) | 90.5 |
| Skimmed milk powder | 2.0 |

TABLE 6-continued

| Ingredients | [%] |
| --- | --- |
| Sugar | 5.0 |
| Culture | 2.5 |

To prepare the yogurt, the milk is heated to 35° C. before addition of milk powder, stabilizer, sugar and isolated *B. fragilis* PSA. This mixture is heated to 65° C. to dissolve all ingredients. Then the mixture is homogenized in a high-pressure homogenizer ($p_1$=150 bar, $p_2$=50 bar) at 65° C. This emulsion is then pasteurized at 80° C. for 20 minutes. After cooling to 45° C., natural yogurt culture is added and mixed. This mixture is then filled into cups and fermented at 45° C. for 3-4 hours until a pH of 4.3 is reached. Cups are then stored at 4° C.

Ice cream (typical serving 85 g) containing 10 mg to 1000 mg per serving isolated *B. fragilis* PSA can be prepared from the ingredients listed in Table 7.

TABLE 7

| Ingredients | [g] |
| --- | --- |
| Milk (3.7% fat) | 600.00 |
| Cream (35% fat) | 166.00 |
| Skim milk powder | 49.10 |
| Sugar | 109.00 |
| Glucose syrup 80% | 70.00 |
| Ice cream stabilizer | 5.00 |
| Flavor | q.s. |
| Color | q.s. |

Sugar, skim milk powder and stabilizer are added to the milk and cream, mixed and heated to 45° C. Then the color, as stock solution, and the glucose syrup is added as well as the isolated *B. fragilis* PSA. The mix is heated and pasteurized (20 minutes, 80° C.). The mix is homogenized, subsequently cooled under constant stirring and the flavor is added at 5° C. The mix is maturated at 5° C. for at least 4 hours and then passed through an ice cream machine (overrun ca. 100%). The ice cream is filled into cups and stored at −20 to −30° C.

What is claimed is:

1. A method for stimulating FoxP3+ regulatory T cell expression of CD39 comprising contacting human FoxP3+ regulatory T cells ex vivo with an effective amount of *Bacteriodes fragilis* capsular polysaccharide A that stimulates expression of CD39 by the FoxP3+ regulatory T cells.

2. The method of claim 1, further comprising contacting the cells with retinoic acid.

* * * * *